United States Patent [19]

Applegate et al.

[11] Patent Number: 5,016,643

[45] Date of Patent: May 21, 1991

[54] VASCULAR ENTOPTOSCOPE

[75] Inventors: Raymond A. Applegate, San Antonio, Tex.; Arthur Bradley, Bloomington, Ind.

[73] Assignee: Board of Regents, The University of Texas System, Austin, Tex.

[21] Appl. No.: 518,065

[22] Filed: May 2, 1990

[51] Int. Cl.[5] ............................................. A61B 13/00
[52] U.S. Cl. .................................... 128/745; 351/209; 351/221; 356/28; 356/39; 128/691
[58] Field of Search ....................... 128/637, 691, 745; 356/28, 39; 351/209, 210, 221, 246

[56] References Cited

U.S. PATENT DOCUMENTS

| | | | |
|---|---|---|---|
| 4,166,695 | 9/1980 | Hill et al. | 356/28 |
| 4,425,924 | 1/1984 | Riva et al. | 128/745 |
| 4,443,075 | 4/1984 | Crane | 351/209 |
| 4,476,878 | 10/1984 | Riva et al. | 128/745 |
| 4,520,816 | 6/1985 | Schachar | 606/4 |
| 4,569,354 | 2/1986 | Shapiro et al. | 128/745 |
| 4,848,897 | 7/1989 | Aizu et al. | 128/691 |
| 4,856,891 | 8/1989 | Pflibsen | 351/210 |
| 4,883,061 | 11/1989 | Aizu et al. | 128/691 |

OTHER PUBLICATIONS

Campbell and Robson, "A Fresh Approach to Stabilized Retinal Images", J. Physiol, (1961), 158:11.
Koppenberg et al., "An Entoptic Method for the Measurement of Eccentric Fixation in Amblyopia ex Anopsia", Am. J. Opt. Arch. Am. Acad. Opt., (1972) 49:417.
Medina et al., "Entoptic Visualization of Foveal Vessels", ARVO Abstract Invest. Ophthal. Vis. Sci., (1986) 27(Suppl):256.
Laatikainen et al., "Capillary-Free Area of the Fovea With Advancing Age", Invest. Ophthalmol. Visual Sci., (1977) 16(12):1154–1157.
Bresnick et al., "Abnormalities of the Foveal Avascular Zone in Diabetic Retinopathy", Arch. Ophthalmol., (1984) 102:1286–1293.
Bligard et al., "Aging Changes of the ParaFoveolar Vasculature: A Trypsin Digest Study", Invest. Ophthalmol., (1984).
Weale, "Why Does the Human Retina Possess a Fovea", Nature (1966) 212:255–256.
Dartnall and Thomson, "Retinal Oxygen and Macular Pigmentation", Nature (1949) 164:876.
Bird and Weale, "On the Retinal Vasculature of the Human Fovea", Exp. Eye Res., (1974) 19:409–417.
Yeung et al., "New Observations on Retinal Microcirculation at the Posterior Pole in Man", Trans. Fourth Asia-Pacific Congress of Ophthal., (1973) 25:155–161.
Kluxen and Wilden, "An Entoptic Test in Diabetic Patients", Diabetes Care (1987) 10(6):800–801.
Helmholtz, Treatise on Physiological Optics (1962):217–218.
Shimizu and Ujiie, Structure of Ocular Vessels (1978):1–14, 16, 18 and 43.
Sharpe, "A Fresh Approach to Stabilized Retinal Images, Part II", J. Physiol., (1971) 217:9–10.
Macular Photocoagulation Study Group, "Argon Laser Photocoagulation for Neovascular Maculopathy", Arch. Ophthalmol., (1986) 104:694–701.

(List continued on next page.)

Primary Examiner—Francis Jaworski
Assistant Examiner—George Manuel
Attorney, Agent, or Firm—Arnold, White & Durkee

[57] ABSTRACT

Described herein are an apparatus and range of techniques used to study the retinal vasculature near the fovea, a description of the need and rationale for noninvasive in vivo monitoring of the retinal vasculature, a presentation of theoretical and practical considerations which demonstrate that entoptic visualization of the smallest capillaries near the fovea is optimized by a small short wavelength source (1 mm or less) rotating at 3.5 Hz in a circular path (radius 2 mm) imaged in the plane of the eye's entrance pupil and a discussion of the feasibility of using these techniques as a research and clinical tool.

93 Claims, 16 Drawing Sheets

A TO $B_1$ = $B_1$ TO $PS_1$
FSM TO $B_2$ = $B_2$ TO SUBJECT
S TO $L_1$ = A TO $L_2$ = $L_2$ TO SUBJECT = 22 cm
$PS_1$ IS MOBILE
$PS_2$ IS STATIONARY

OTHER PUBLICATIONS

Macular Photocoagulation Study Group, "Argon Laser Photocoagulation for Ocular Histoplasmosis", Arch. Ophthalmol., (1983) 101:1347–1357.

Macular Photocoagulation Study Group, "Argon Laser Photocoagulation for Idiopathic Neovascularization", Arch. Ophthalmol., (1983) 101:1358–1361.

Macular Photocoagulation Study Group, "Krypton Laser Photocoagulation for Neovascular Lesions of Ocular Histoplasmosis", Arch. Ophthalmol., (1987) 105:1499–1507.

Han et al., "Visual Loss After Successful Photocoagulation of Choroidal Neovascularization", Ophthalmol., (1988) 95:1380–1389.

Zeffren et al., "Retinal Fixation Point Location Within the Foveal Avascular Zone", In Press, Invest. Ophthalmol. and Visual Sci.

Applegate et al., "Entoptic Visualization of the Retinal Vasculature Near Fixation", In Press, Invest. Ophthalmol. and Visual Sci.

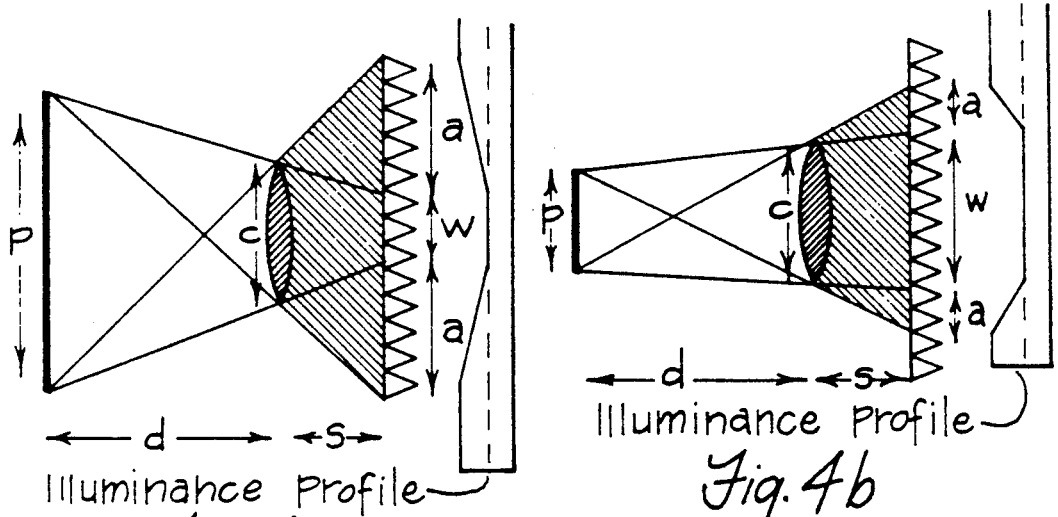
Illuminance Profile
Fig. 4a
Illuminance Profile
Fig. 4b
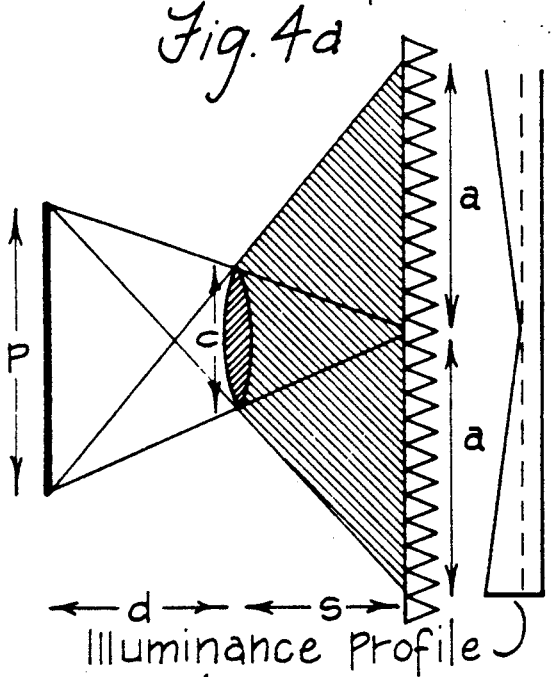
Illuminance Profile
Fig. 4c
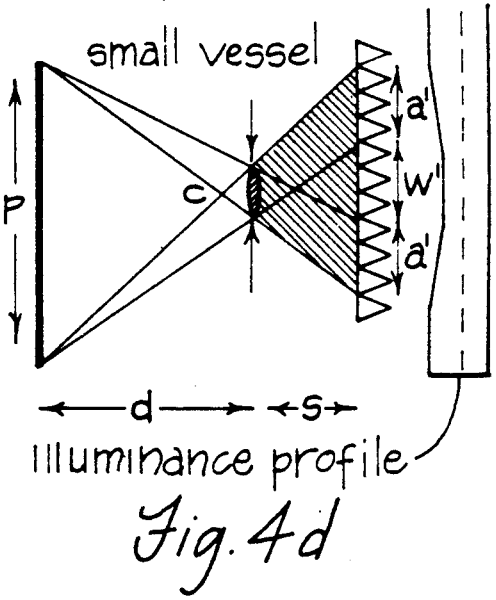
small vessel
Illuminance profile
Fig. 4d A TO $B_1$ = $B_1$ TO $PS_1$
FSM TO $B_2$ = $B_2$ TO SUBJECT
S TO $L_1$ = A TO $L_2$ = $L_2$ TO SUBJECT = 22 cm
$PS_1$ IS MOBILE
$PS_2$ IS STATIONARY

VASCULAR ENTOPTOSCOPE

Research relating to the development of the present invention was supported in part by grants from the United States Department of Health and Human Services (NIH EY08005 and EY07638). The United States government may have corresponding rights to the license and use of any resulting patent.

BACKGROUND OF THE INVENTION

The present invention relates to use of a psychophysical method and apparatus for entoptically evaluating and mapping the human foveal area vasculature with respect to the retinal point of fixation (RPF). Knowing the location of the RPF is essential in modern ophthalmic surgery because it can be inadvertently damaged during photocoagulation, resulting in marked vision loss. Unfortunately, the RPF is not visible on direct examination of the eye; its location must be determined subjectively and then related to observable landmarks. The present invention uses well-known techniques of entoptic visualization in a novel way to accomplish this goal.

While entoptic (referring to visual phenomena having their seat within the eye) observations of retinal vessel shadows were recorded more than 100 years ago, these subjective sensations have thus far found limited use in modern medical practice. In part, this is because convenient objective photographic methods have been developed for studying the retinal vasculature, thus relegating subjective observations (with their lack of objective controls) to a secondary role. In practice, for example, entoptic perceptions of the geometric patterns of blood vessels have been described only schematically, while fluorescein angiography has produced a wealth of detailed photographs. But what is lacking in the photographs (and other direct observations) as well as the entoptic perceptions to date is quantification of the location of the RPF with respect to the vasculature architectures.

Instead of the RPF, what is evident on most retinas (and what is usually assumed to be concentric with the RPF) is the foveal avascular zone (FAZ), an area surrounding the fovea where retinal vessels are absent or decreased. Recent research has shown that the FAZ and the RPF are not, as previously assumed, always concentric. The assumption has persisted because it is approximately correct in most people and, prior to the present invention, there was no convenient way to check it in a given patient. Now that a simple, accurate mapping system has been developed and tested, there are data to suggest that therapeutic failures following photocoagulation (defined as loss of 6 or more lines of visual acuity) may be reduced up to 20% in specific groups of patients having preoperative mapping of the retinal vasculature with respect to the RPF.

Studies of the Foveal Avascular Zone (FAZ)

Techniques to study the FAZ can be classified into 3 categories: anatomic, angiographic, and psychophysical. Anatomic studies in human and other primates include whole mount and flat mount following trypsin digestion, and injection with india ink, neoprene latex and derivatives of methacrylic esters. While anatomic studies often provide eloquent detail of the vasculature surrounding the foveal area, they do not allow in vivo monitoring of changes in the vasculature and may be misleading. For example, latex injection under pressure may open anatomic connections which are not operative under normal physiologic conditions.

Fluorescein angiography, on the other hand, is generally accepted as the standard procedure for in vivo study of the human retinal vasculature, but it is invasive and not generally repeated daily or even weekly. Furthermore, to obtain the capillary detail necessary to study the FAZ and the vasculature near the fovea requires clear optical media and skilled photographic personnel. And even if photographic conditions are ideal, the angiographic detail of the foveal area vasculature may be variable in quality, depending on the density of the macular pigment and variations in normal fundus pigmentation.

Nevertheless, fluorescein angiography as well as angiography with other dyes have been used extensively to study the retinal vasculature and FAZ in both healthy and diseased eyes in vivo. Laatikainen and Larinkari (1) reported FAZ diameters around 0.57 mm for 167 eyes of 158 healthy patients (mean=0.572, range 0.23 mm to 0.83 mm). Bresnick et al. (2), in a study of the FAZ in diabetics, reported FAZ diameters between 0.58 and 1.00 mm with a mean of 0.73 mm for the normal control group (non-diabetic). Together these findings are consistent with the anatomic findings of Bligard et al. (3) where post-mortem human eye FAZ diameters were reported to range from 0.12 to 1.2 mm (mean 0.65 mm) using trypsin-digest. In diseased eyes, the FAZ has been reported to be smaller than normal in patients with cicatricial retinopathy of prematurity and larger than normal in vascular occlusive diseases such as diabetes, sickle cell retinopathy, talc embolic retinopathy and retinal branch vein occlusion. Taken together, all of these data provide a basis for comparison with retinal maps made possible by the psychophysical techniques of the present invention. Psychophysical procedures, however, can provide data unobtainable with angiography.

For example, even in the presence of cloudy ocular media, viewing a bright uniform blue field (430 nm) allows the entoptic visualization of leucocytes ("flying corpuscles") in the retinal capillaries surrounding the foveal area. Careful observation of the phenomenon reveals an area apparently centered on the RPF where no leucocytes are seen; presumably the FAZ. Yap et al. capitalized on this phenomenon to measure, in one eye of 22 normal subjects, FAZ diameters ranging between 1.92 and 2.86 degrees (0.59 to 0.83 mm on the retina assuming a secondary nodal point-to-retina distance of 16.67 mm). Earlier estimates using the same entoptic phenomena found the diameter of the FAZ to be approximately 1.5 degrees as measured in object space or 0.44 mm on the retina (Weale (4) quoted by Dartnall and Thomson (5)). But, while entoptic visualization of leucocytes provides a non-invasive method for making inferences about the FAZ and the vasculature of the foveal area, it does not provide a view of the retinal vessels themselves.

Direct entoptic visualization of the retinal vasculature can be achieved by allowing light to enter the eye from unusual or constantly varying angles. This effect, first noted by Purkinje in 1819 (6), is strikingly distinct and often spontaneously reported by patients during routine ophthalmoscopy. Bird and Weale (7), using both fluorescein angiography and entoptic visualization of the retinal vasculature by scleral trans-illumination, noted that not all normal individuals with excellent visual acuity have FAZs which are truly avascular. They point out that unless extreme care is taken during the entire photographic process, vascular details within the FAZ may not be imaged (or seen) with fluorescein angiography but are visible entoptically. These findings corroborate the earlier fluorescein angiographic work of Yeung et al. (8) and emphasize the potential sensitivity of entoptic viewing of the central retinal vasculature.

Clinically, entoptic visualization has long been used to help evaluate the functional status of the retina behind obstructed media. More recently it has been used as a guide to train eccentric fixators to improve fixation, and to study the normal variation in the size and shape of the FAZ. To the best of the present inventors' knowledge, only one study has used entoptic visualization to monitor an active disease state. Kluxen and Wilden (9) taught 136 insulin-dependent diabetics how to observe their retinal vasculature entoptically. In patients with 1-5 microaneurysms, as revealed by fluorescein angiography, 55% could entoptically detect their own pathology. In patients with 6-20 microaneurysms the percentage increased to 77%. In patients with greater than 20 microaneurysms with severe background and proliferative retinopathy, 90% could reliably detect their own pathology and many could document the appearance of new and disappearance of old microaneurysms over time.

While entoptic visualization of the retinal vasculature is impressive in its apparent detail, capturing this detail in a quantifiable manner is difficult. First, entoptic visualization is subjective by nature. Second, foveation of the variety of intricacies of the vascular detail is impossible because the entoptic image remains fixed with respect to the retina (i.e, the location of the retinal vasculature is fixed with respect to the photoreceptors; therefore, eye movements cannot foveate the vessel of interest.). Together these effects have limited the usefulness of this phenomenon. To minimize these problems, the present invention includes an attempt to enhance stimulus effectiveness by presenting the test stimulus in Maxwellian view and optimizing stimulus movement. The use of Maxwellian view for entoptic visualization of the retinal vasculature was first alluded to by Helmholtz (10) in his *Treatise on Physiological Optics* where, in discussing entoptic visualization of the retinal vasculature, he said:

> The. . . vascular figure may be seen also by looking through a compound microscope with nothing upon the stage, the background being the uniformly bright circular aperture of the diaphragm. When the eye moves to and fro a little at the ocular, the slender retinal blood vessels appear sharply delineated in the field, particularly those running at right angles to the direction of the motion, whereas the others vanish that are parallel to this direction.

Helmholtz goes on to point out the importance of the size of the Maxwellian view exit pupil on shadow formation by stating:

> If the pupil is perfectly free, and the eye is turned towards the bright sky, every point of the pupillary plane may be considered as a source of light sending rays in all directions to the fundus of the eye, just as if the pupil itself were a luminous surface. The result is that the blood vessels of the retina project broad hazy shadows on the parts of the retina immediately behind them, the length of the umbra being only about four or five times the diameter of the blood vessel. . . . Hence it may be assumed that the umbra of the vascular shadow does not reach the posterior surface of the retina at all. But when the light enters the eye through a narrow aperture in front of the pupil, the shadow of the blood vessel is necessarily smaller and more sharply defined, and since the umbra is longer, parts of the retina that were formerly partially shaded are now completely shaded, while other adjacent parts are not shaded at all.

Thus, the principles of entoptic visualization have been described, but prior to the present invention, no device had been built or proposed to optimize the patient's view of the retinal vessel pattern surrounding the RPF and locate the RPF precisely on a retinal map. The need for this information, however, is substantial and growing.

Such data would be particularly useful for eye surgeons who, during photocoagulation therapy, focus high power laser beams on the retina by using the retinal vessels as landmarks. It is most important for the surgeon to avoid burning the retinal point of fixation (to avoid vision loss), but that point is subjectively determined by the patient in all cases and cannot reliably be assumed to lie at the center of the FAZ or the anatomical fovea. Thus, the present invention fills an important need and provides a significant safety factor for the increasing number of patients who could benefit from foveal area photocoagulation therapy.

Anatomy and Shadows Within the Eye

Within the portion of the retina resting on the choroid (pars optica), several layers can be distinguished; FIG. 1 shows them schematically. At the posterior pole, the distribution of retinal components is altered to form highly specialized structures which maximize visual acuity, the anatomical fovea and foveola. In the center of the fovea, the inner retinal layers down to the outer nuclear layer are displaced, forming a pit, the foveola, which contains the highest density of cones in the retina (147,000 cones per square mm). The retinal capillaries of the area of the fovea typically form concentrically arranged channels ending in a capillary loop approximately 0.5 mm across which outlines a capillary-free zone, the FAZ. The lateral displacement of inner retinal structures, including the retinal vasculature, presumably exists to leave an unobstructed light path to the site of phototransduction, thereby enhancing image quality.

In a normal observer, visual performance is maximized at the subject's point of fixation. That is, when asked to fixate a point in space, normal observers move their eyes such that the point of interest is imaged on the retinal region providing the highest resolution. The connection between fixation and optimal resolution, together with the histological specialization of the retina, suggest that a normal individual will move the eye to place the image of the RPF on the foveola. Thus the RPF and the foveola are commonly assumed to be coincident and reasonably centered in the FAZ. But, experimental use of the present invention has brought this assumption into sharp question for a significant minority of patients. Using the methods and apparatus taught herein, these patients may be identified and their treatment appropriately modified to maximize preservation of vision. The guideposts in this process are vascular shadows subjectively perceived by the patient and their relationship to the RPF.

Since the retinal vasculature lies anterior to the photoreceptors, shadows of the vasculature are cast in the plane of the photoreceptors. Under normal viewing and lighting conditions the vascular shadows of all but the largest vessels have low contrast and all are effectively stabilized with respect to the photoreceptors. Since patterns which are stabilized in the plane of the receptors fade and become invisible, vascular shadows are not perceived under normal lighting and viewing conditions.

Entoptic visualization of the vascular shadows can be achieved by increasing shadow contrast and breaking shadow stabilization. Contrast can be increased by placing a small light source in the eye's entrance pupil and shadow stabilization can be broken by changing the retinal angle of incident light by constantly moving the light source. There are at least four parameters of the vessel shadow pattern in the plane of the entrance aperture of the photoreceptors which will effect shadow visibility: (1) the width of the shadows; (2) the contrast of the shadows; (3) the spacing of the shadows; and (4) the speed, and path of shadow movement. In the present invention, the first goal was to design an illumination procedure that optimizes these parameters and renders the vascular bed surrounding the fovea easily visible.

SUMMARY OF THE INVENTION

The present invention includes an apparatus for entoptically perceiving and mapping the foveal area vasculature of the retina of a human subject's eye. The apparatus comprises a means to establish and maintain translational and rotational alignment of said eye with said apparatus. Such means may be an affixed bite bar preferably of dental impression-type material for a subject to orally embrace or a chin rest alignment ring and monitoring system. There are numerous eye tracking systems which could be modified and employed to meet this instrumentation need. The apparatus has a main light source (preferably of variable intensity and shape) which is imaged in or near an entrance pupil plane of the eye and a means of moving said main light source or image of the main light source along a path in space. The main light source has a peak wavelength of about 430 to 555 nm (preferably about 470 nm) and a half band pass of approximately +/− 60 nm. The main light source image is preferably circular and has a diameter of approximately 0.5 to 3 mm (preferably 1.0 mm or less). The main light source is imaged in or near said eye's entrance pupil plane or anterior focal plane. The main light source image is preferably of uniform intensity. This main light path is preferably circular and 2 to 6 mm, (more preferably 4 mm) in diameter. The main light path is retraced at a rate of 0.5 to 10 Hz (preferably 3.5 Hz).

The apparatus further includes means of directing the main light image into the eye's entrance pupil, resulting in the angle of illumination of said eye's retina changing with time (preferably in a circle). There are several available ways to image the main light source in the eye's entrance pupil. This can be accomplished as described with lenses, or it can be done with mirrors, or a combination of both.

Also in the apparatus are means to image an aperture at optical infinity or any other plane of interest (e.g., to correct for refraction error of the subject) as an optical field stop for said apparatus. There are several available ways to image the imaging on aperture source in the eye's entrance pupil. This can be accomplished as described with lenses, or it can be done with mirrors, or a combination of both. This aperture is of variable size and shape and preferably is an iris diaphragm.

The apparatus additionally has a fixation light source and a means to form an image of the fixation light on the retina of the eye. The fixation light source is preferably of variable intensity. The fixation light retinal image is within (preferably centered) the circle described by the field stop. There are several available ways to image the fixation light source in the eye's entrance pupil. This can be accomplished as described with lenses, or it can be done with mirrors, or a combination of both.

A tracking light source and a means to form an image of the tracking light on the retina of said eye are also part of the apparatus. The tracking light source is again preferably of variable intensity. Additionally included in the apparatus is a means of moving the tracking light retinal image with respect to the fixation light retinal image. The means of moving said tracking light retinal image is a device such as a joy stick or similar x-y manual controller. There are several available ways to image the tracking light source in the eye's entrance pupil. This can be accomplished as described with lenses, or it can be done with mirrors, or a combination of both. In addition, in some applications it may be advantageous to have the fixation and tracking point sources be dots on a CRT (computer screen). This would provide several advantages in documentation as well as serving as a means for creating the comparator for blood flow measurements.

An important apparatus component is a means of transducing movement of the tracking light retinal image to yield coordinates of its present location on retina with respect to the location of the fixation light retinal image. The location can be kept track of using several different methods. In principal, all that is necessary is to keep track of the point source movement (or point source image movement) and correct for the optics of the eye and apparatus. This can be done using a computer, or mechanical and/or optical methods. The tracking light retinal image coordinates are calibrated in units of length measured on said retinal surface or units of angular subtense.

To achieve the desired results, the apparatus includes a means of compiling or displaying coordinates of the tracking light retinal image movement. Depending on the user's desires, computer programs can be written by those skilled in the art to compile and display the tracking light location in any manner desired. This compilation or display comprises a map of the tracking light retinal image positions with respect to the fixation light retinal image.

Finally, the apparatus includes a means to detect and indicate magnitude and direction of translation of the eye with respect to the apparatus. There are numerous eye tracking systems which could be modified and employed to meet this instrumentation need. This indication of magnitude and direction of translation of the eye with respect to said apparatus is visible or is sensed by an external operator or computer.

The apparatus of the present invention for entoptically perceiving and mapping the foveal area vasculature in the retina of a human subject's eye may also be modified for concomitantly studying white blood cell circulation through the retinol vasculature. In such modification, the apparatus also comprises a blue-field light source and a means to illuminate the retina with the blue-field light source. This blue-field light source is preferably of variable intensity. For this purpose, the modified apparatus further comprises a speed-comparator light source for casting an image and a means to form a retinal image of the speed-comparator light on the retina. This speed-comparator light source is preferably of variable intensity and the speed-comparator light source retinal image a size about equal to entoptically perceived white blood cells.

Additionally, such a modified apparatus includes a means of causing said speed-comparator light retinal image to move along a path having a variable length and curvature on the retina at a fixed velocity.

Lastly, the modified apparatus includes a means of rotating and translating the speed-comparator light retinal image on the retina. This, and the immediate means are of types commonly known to those of skill in this area.

The blue-field light source has a characteristic wavelength of about 430 to 500 nm, is directed coaxially with light from the fixation light source, comprises approximately 50% of total light, and is applied to said retina constantly or intermittently at a frequency of about 50 to 60 Hz.

The retinal path of the speed-comparator light image is straight or curved to mimic the course of a retinal vessel and has a length of about $10^{-3}$ to $10^{-2}$ m. The velocity of the speed comparitor can be adjusted to mimic velocity of a white corpuscle passing through vasculature.

The present method for entoptically perceiving and mapping the foveal area vasculature in the retina of the eye of a human subject under examination with respect to the retinal point of fixation involves the use of the above apparatus and may be described as follows.

Initially a main light source image of variable intensity is directed within the eye's entrance pupil to illuminate a portion of the retina defined by a field stop.

The main light source image is moved along a main light path in space which results in the angle of retinal illumination changing with time. A fixation light source of variable intensity is then imaged on the retina to form a retinal image of the fixation light. The subject is directed to visually fixate on the fixation light. The subject reports descriptions of entoptically perceived vascular features of interest near the eye's foveal area.

A tracking light source is directed on the retina to form thereon a retinal image of the tracking light which is variable in intensity and movable over the retinal surface with respect to the above fixation retinal image. This is accomplished through use of a tracking light controller operated by the subject. The fixation light and tracking light source images are viewed by the eye through an optical field stop aperture illuminated by the main light, this aperture is imaged at infinity or other plane of interest. Outputs of the tracking light controller are scaled to correspond to distances on the retinal surface of the eye and/or angles subtended at the first nodal point of the eye.

The subject is directed to and does move the tracking light retinal image along or around entoptically perceived vascular features of interest while maintaining constant translational and rotational alignment of the eye with the fixation light retinal image.

Using scaled outputs of the tracking light controller position reports are created of entoptically perceived vascular features of interest on the retina. These position reports are combined with descriptions of said entoptically perceived vascular features of interest to create a retinal vascular map.

The intensities of the main, fixation and tracking light sources are adjusted for best entoptic visualization, as are the frequency of rotation and thus velocity of the main light source image.

The eye is observed to detect misalignment with the instrument or loss of proper fixation due to any combination of translation or rotation. Corrections are determined as required of said position reports resulting from said misalignment of the eye with the instrument of loss of fixation and these corrections are applied to the position reports.

This method for entoptically perceiving and mapping the foveal area vasculature in the retina of the eye of a human subject under examination with respect to the retinal point of fixation may be modified to perceive white blood circulation. The modified method includes illuminating the retina intermittently or constantly with a blue-field light source of variable intensity and, if intermittent, having a duty cycle of less than 100%. The subject reports perceived entoptic perception of said white blood cell circulation. The subject adjusts the intensity of the light sources for best entoptic perception.

BRIEF DESCRIPTION OF THE DRAWINGS

FIG. 4 shows schematics illustrating the interaction of source size, and vessel location and size, on the illuminance profile of the vessel shadow in the plane of the entrance aperture of the photoreceptors. P denotes the source diameter in the exit pupil of the eye, and represents the uniform portion of the illuminance profile having maximal contrast (umbra), a illustrates the penumbra portion of the shadow (ramping illuminance profile) and w represents the portion of the shadow with a uniform illuminance profile of less than maximal contrast. Parameters c, d, s and w are defined in FIG. 3. Panel A is used as a reference to illustrate the effects of decreasing the size of the source P (Panel B), increasing the distance s (Panel C) and decreasing the vessel size c (Panel D).

DESCRIPTION OF THE PREFERRED EMBODIMENT

Modeling Assumptions

While a full treatment of the optical properties of the retinal blood vessels would deal with absorption, focusing, and scattering by the blood vessel walls, the blood plasma, and the individual red and white corpuscles, as well as diffraction effects, an excellent description of the entoptic perception of the retinal vessels near the RPF may be provided using a model based on absorption and the geometric optics of shadow formation. Therefore, for the present model the optical consequences of focusing, scattering and defraction are ignored in favor of a model based on absorption and geometric optics.

1. Shadow Width

Figure 2:
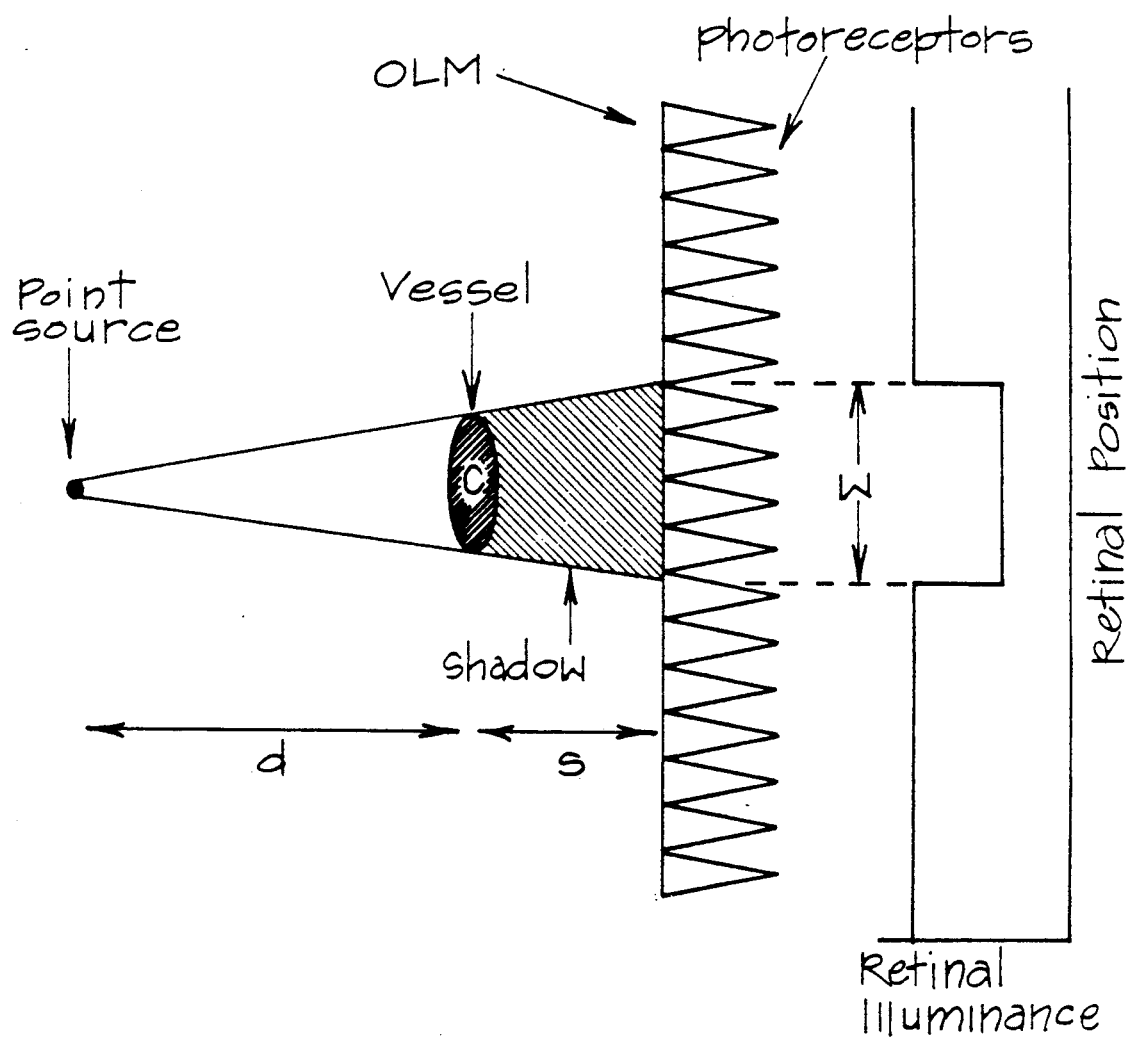
FIG. 2 is a point source illumination of a vessel c from a distance d forming a shadow with a rectangular illuminance profile of maximal contrast with a width w in the plane of the photoreceptor's entrance aperture assumed to be the outer limiting membrane (OLM) a distance s from the capillary.

Using geometrical optics, shadow width as seen at the photoreceptor entrance aperture, here defined to be the outer limiting membrane (FIG. 2), depends on four key elements: (1) the width of the vessel, c; (2) the distance from the vessel to the entrance aperture of the photoreceptor, s; (3) the distance from the illumination source to the vessel, d; and (4) the size of the source illuminating the vessel, P.

1.1 Vessel Width.

Detailed histological data from human eyes provide estimates of diameter for arteries (100 microns), veins (180 microns), arterioles (21 microns), venules (23 microns), and capillaries (7 microns). Shimizu and Ujiie (11) contend that capillaries may be slightly larger at the border of the foveal avascular zone (10 to 15 microns).

1.2 Distance from the Vessel to Photoreceptors

Figure 1:
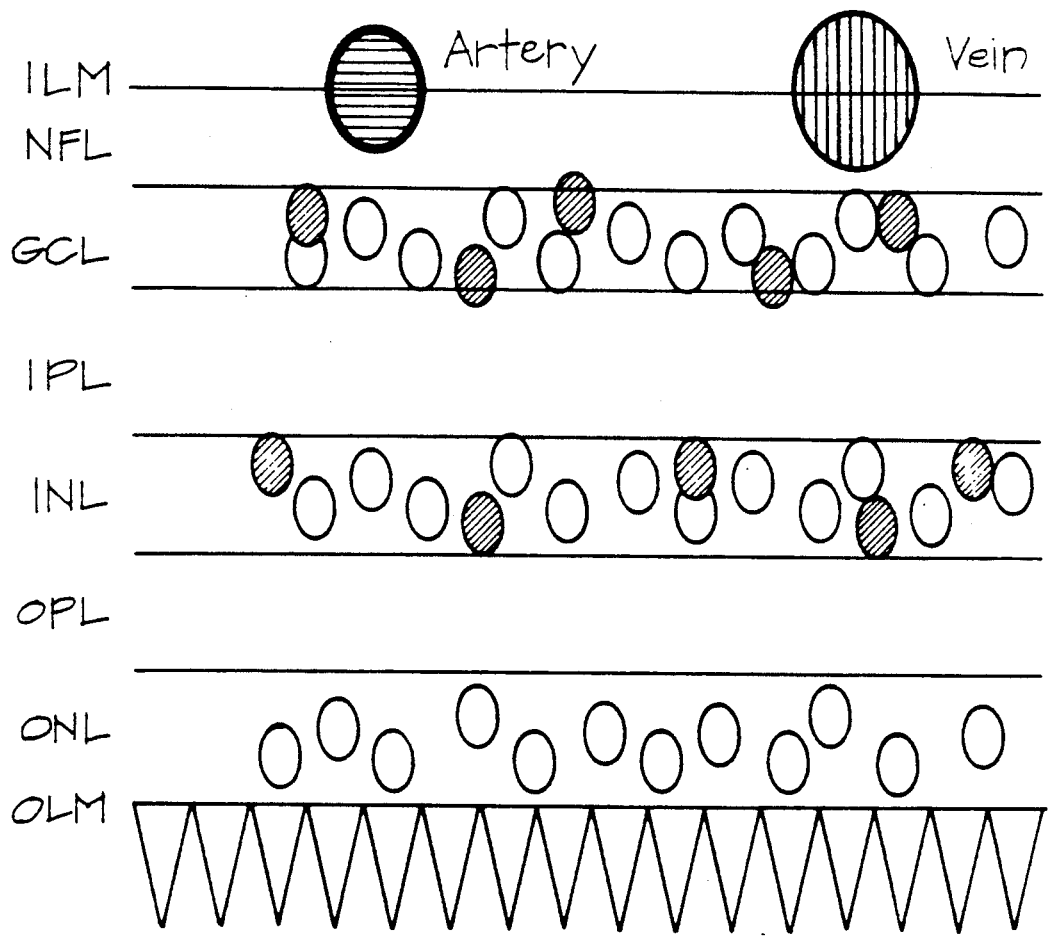
FIG. 1 is a schematic illustration of the location of vessels (solid ovals) within the various layers of the retina. Inner limiting membrane (ILM), neural fiber layer (NFL), ganglion cell layer (GCL), inner plexiform layer (IPL), outer plexiform layer (OPL), outer nuclear layer (ONL), outer limiting membrane (OLM). Direction of light entering the eye is from top of diagram to bottom.

In general, the major arteries, veins, arterioles and venules lie in the nerve fiber layer (NFL), and the capillaries are distributed from the inner limiting membrane (ILM) down into the inner nuclear layer (INL) (FIG. 1). However, the precise distribution of the capillaries is controversial. It has been suggested that they are either evenly distributed or that they are concentrated in two laminae. Despite the disagreement over the precise distribution of the capillaries, collectively, these reports set the range of the distribution of vessel location as the ILM and outer plexiform layer (OPL) border. Therefore, around the foveal region, the retinal vessels will be considered to lie between 300 and 80 microns from the entrance aperture of the photoreceptors. Hereafter, for readability the entrance aperture of the photoreceptors will be referred to simply as the photoreceptors.

1.3 Source Distance

Figure 3:
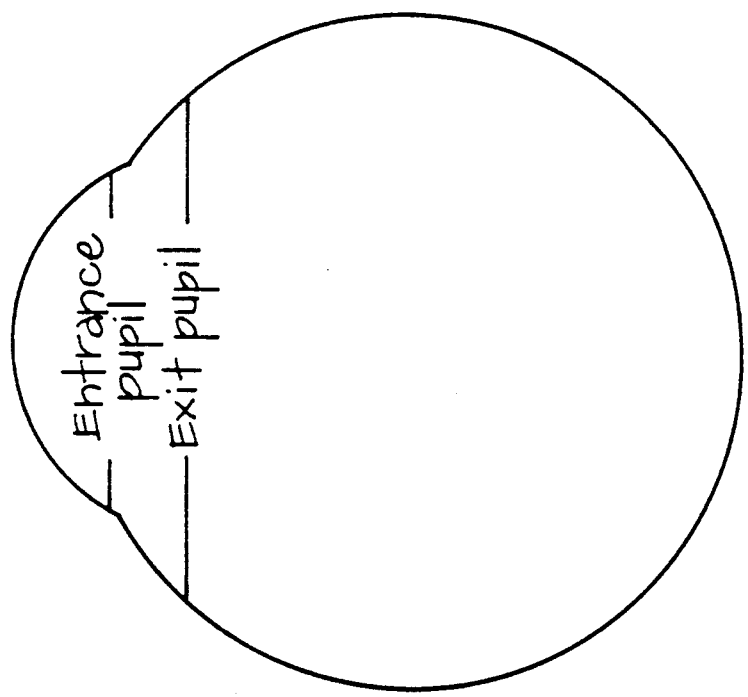
FIG. 3 shows the location of the entrance pupil of the eye with respect to the corneal apex and location of exit pupil of the eye with respect to the plane of the photoreceptors entrance pupil.

The exact distance from the illuminating source to the vessels (d in FIG. 2) is not important in determining shadow size in cases where the distance d is considerably larger than the distance s from the vessels to the photoreceptors. Nevertheless, to calculate accurately the width of the vascular shadows for a variety of capillary locations, the distance d needs to be defined for each capillary location. This can be done by defining the location of the source (or source image) and adopting the optical parameters of a schematic eye. If the eye is assumed to be Gullstrand's simplified schematic eye and the eye's iris (the aperture stop of the eye) is placed on the anterior surface of the crystalline lens, then the distance from the eye's exit pupil to the photoreceptors is 20.49 mm (FIG. 3). Combining these assumptions with the knowledge that distance from the capillaries to the photoreceptors ranges from 80 and 300 microns, the distance d varies from 20.410 mm for capillaries at the INL to 20.190 mm for capillaries in the ILM. Given these parameters, and assuming the source is a point source in the plane of the entrance pupil, the retinal shadows of the vessels will have a rectangular illumination profile and, at the outer limiting membrane, will be slightly wider (0.4–1.5%) than the vessels themselves. Alternatively, if we had placed the point source at the anterior focal point of the eye, then light after refraction by the eye would be collimated and the shadows cast would be the same width as the vessels. By similar triangles in FIG. 3, the shadow width (w) in the point-source case is given by $$width\ of\ shadow = w = (s+d)c/d$$

where c is vessel diameter. It is clear from this analysis that the shadow from the smallest capillaries (7 microns) is larger than the diameter of one photoreceptor (approximately 2 microns). Unfortunately, a point source considerably smaller than 7 microns is difficult to create. If the source is large compared to the size of the vessel, which in any real apparatus it will be, then the illuminance profile of the shadow is no longer rectangular.

1.4 Size of the Source

Figure 5:
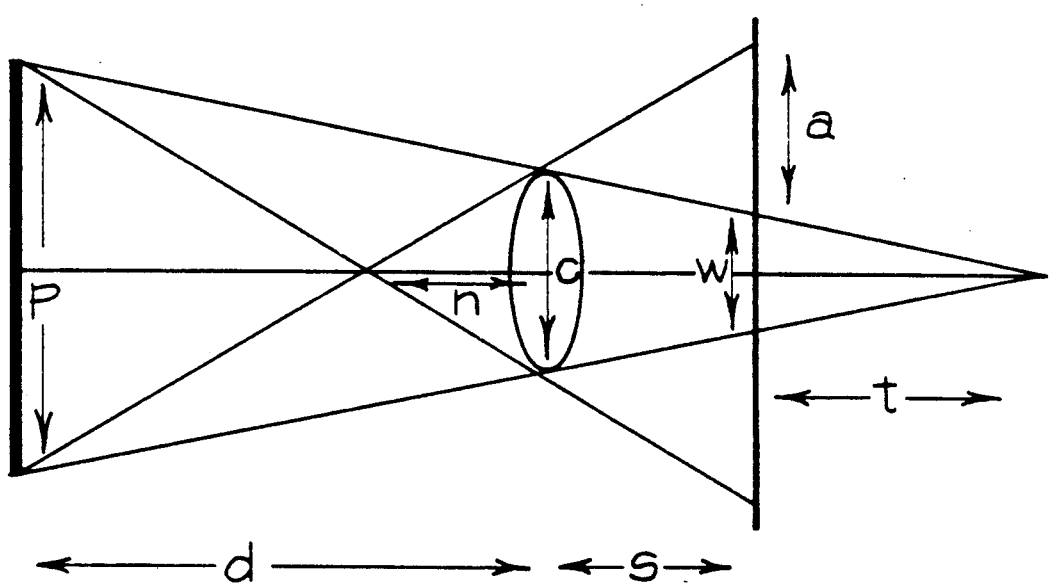
FIG. 5 is a schematic diagram purposely distorted to illustrate the geometric relationships of shadow formation which define shadow width and the nature of the illuminance profile. Parameters defined in FIGS. 2 and 4.

When the light source has a finite diameter P, there is in general an umbra, a region of total shadow (darkly shaded area in FIG. 4), and a penumbra, a region in which the source is partly eclipsed by the vessel (lightly shaded). The illuminance profile in the shadow may or may not contain an area of total shadow (umbra) in the plane of the photoreceptors (FIG. 4). When an umbra is present in the plane of the photoreceptors, (FIG. 4A and 4B), illuminance is a minimum over a central uniform area, then increases through the penumbral regions. As P or s increases, or c or d decreases, the width of the umbra in the plane of the photoreceptors can decrease to zero (FIG. 4C). As a further change in this direction is made, by further increasing source diameter P for instance, no photoreceptor will be hidden from the entire source by the vessel. However, a region of uniform illuminance will again appear (FIG. 4D). This region is less darkened than the actual umbra, and its illuminance will approach that of the background as P continues to increase. Using similar triangles (FIG. 5), the width of the umbral region w in the extended source case is given by $$w/t = c/(s+t) = P/(d+s+t)$$

$$w = (Pt)/(d+s+t)$$

and the width of the penumbra on each side of the central uniform area a is given by $$a/s = p/d$$

$$a = Ps/d$$

Figure 6A:
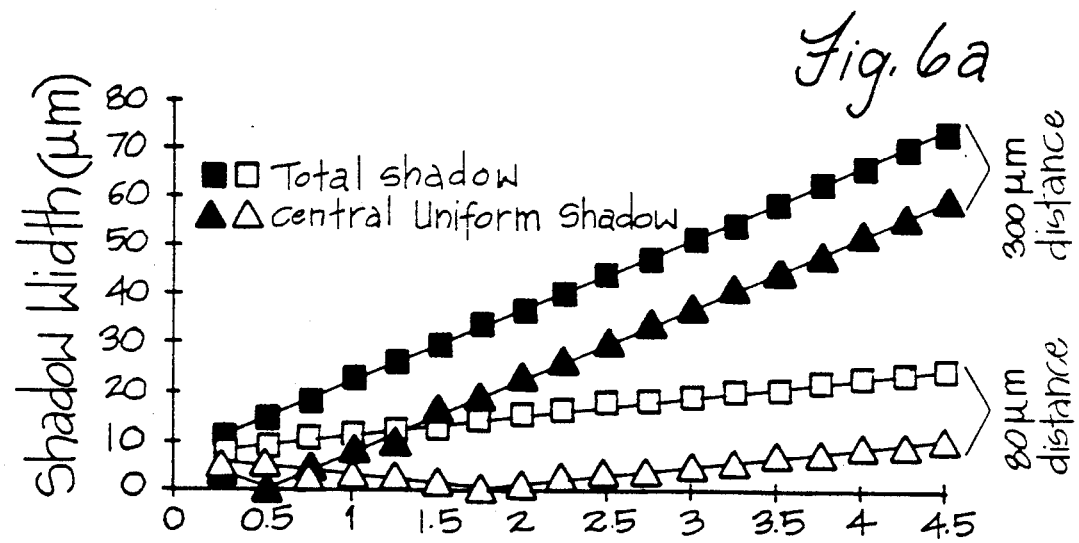
FIG. 6 shows predictions of the effect of source diameter on shadow width (panel A), shadow contrast (panel B) and retinal illuminance (panel C) for 7 micron capillaries positioned at the ILM (300 microns distance) or at the INL (80 micron distance).
Figure 6B:
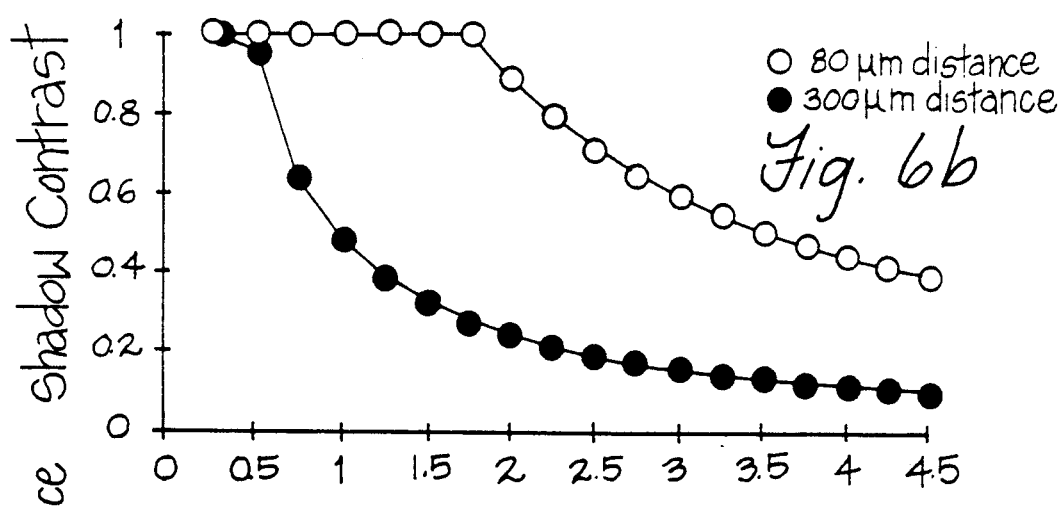
Figure 6C:
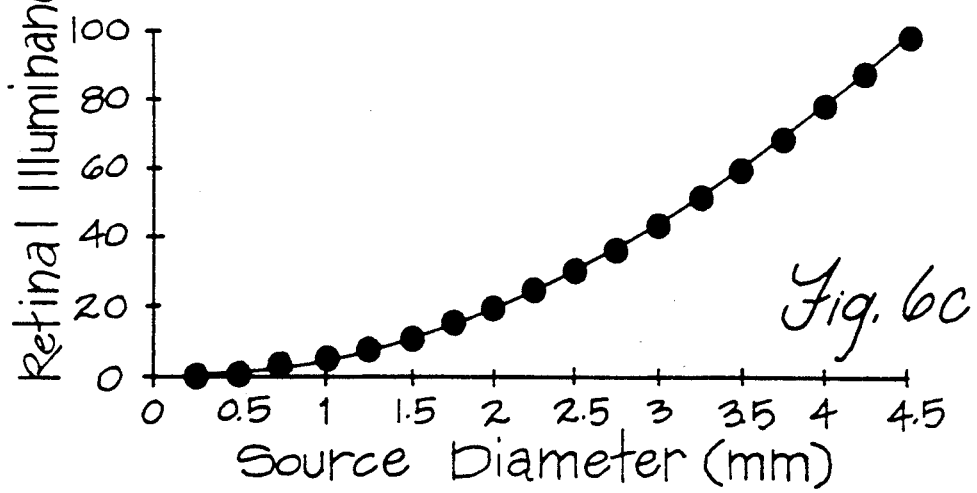

Small changes in the diameter of the source image P in the plane of the pupil will have a marked influence on shadow width, shadow contrast and mean retinal illuminance. FIG. 6 illustrates these three points. FIG. 6A displays the variation in the total width of the shadow (squares) and the width of the central uniform portion of the shadow (triangles) as a function of source diameter for a 7 micron capillary located either 300 (solid symbols) or 80 microns (open symbols) from the receptors. Notice in FIG. 6A, that while the total shadow width (squares) is always greater than the width of a foveal cone (approximately 2 microns) and increases monotonically with source diameter, the width of the uniform portion of the illuminance profile (triangles) first decreases and then increases with source diameter. The initial decrease in the width of the uniform portion of the illuminance profile corresponds to the umbra portion of the shadow moving anterior to the plane of the photoreceptors. At the point where the uniform portion of the illuminance profile goes to zero and starts to increase, maximum contrast of the shadow begins to decay. These effects of source size on image contrast are illustrated in FIG. 6B for a 7 micron capillary located either 300 (closed circles) or 80 (opened circles microns in front of the photoreceptors. Examination of FIG. 6B reveals that increasing the source size beyond 0.5 mm will reduce shadow contrast for the smallest capillaries near the ILM (300 micron distance); however, shadow contrast will remain high for larger vessels or for those capillaries located nearest to the photoreceptors until the source diameter exceeds 1.75 mm. FIG. 6C illustrates the typical limitation of most Maxwellian view illumination systems. That is, for a constant source luminance, reductions in source area (i.e., a decrease in the size of the exit pupil of the Maxwellian view optical system) produces proportional reductions in retinal illuminance. For a circular Maxwellian view exit pupil, retinal illuminance will be inversely proportional to $r^2$. Thus a tradeoff exists. Decreases in source size will increase shadow contrast but decrease retinal illuminance. The former will increase the contrast of the shadow and the latter will decrease the retinal sensitivity to contrast.

Given these three considerations, shadow width, shadow contrast and retinal illuminance, combined with out desire to keep the worst case shadow contrast at least 5 times threshold (see shadow contrast below), we set the source diameter P at 1 mm for modeling purposes.

Figure 7A:
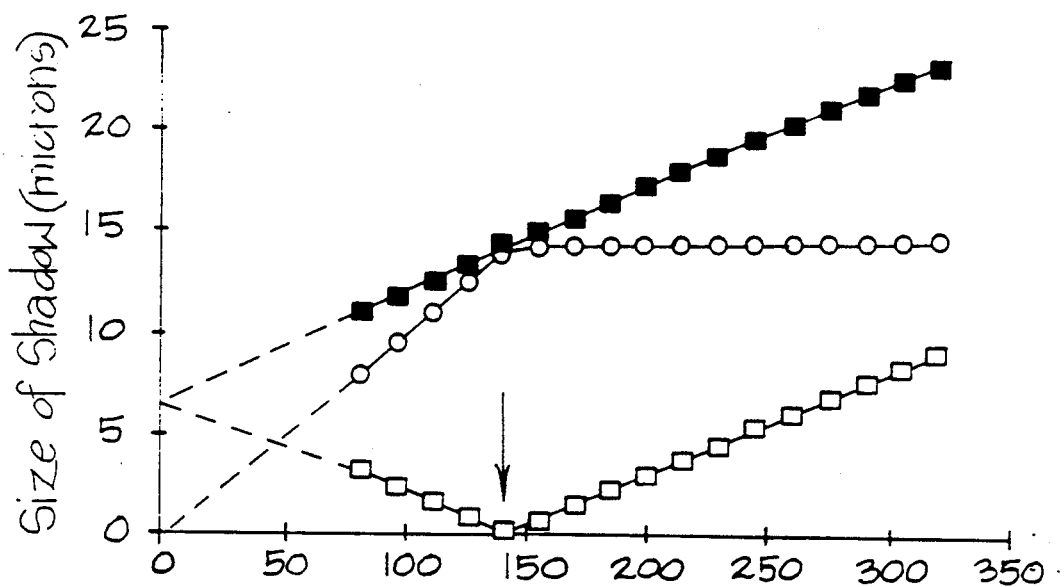
FIG. 7, panel A illustrates total shadow width (solid squares) as well as the width of the uniform (open squares) and ramping (open circles) portions of the shadow formed by a 7 micron capillary as a function of vessel location; panel B shows normalized shadow contrast for a 7 micron (solid squares) and 14 micron (open squares) capillary as a function of vessel location. Retinal layers OPL, INL and OLM refer to the outer plexiform layer, the inner nuclear layer and the outer limiting membrane, respectively.
Figure 7B:
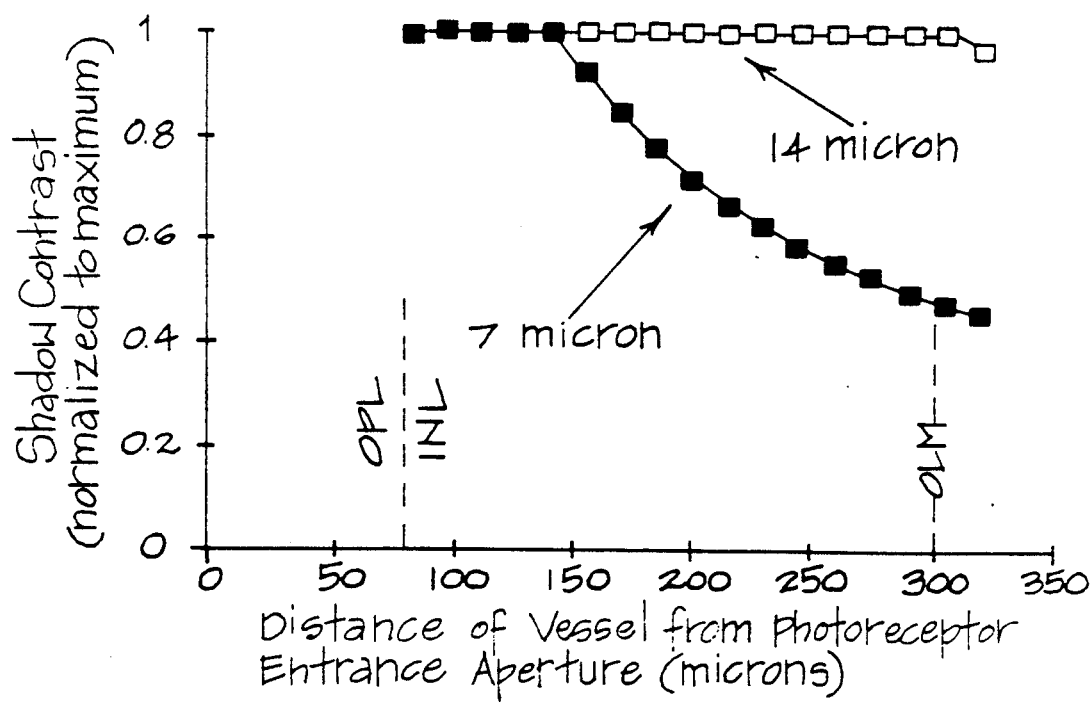

FIG. 7A illustrates the width of (1) the uniform portion (open squares), (2) the ramping portion (open circles), and (3) the total width (solid squares) of the illuminance profile in the plane of the photoreceptors as a function of vessel distance from the photoreceptors. There are several important points illustrated by this figure. First, notice the total shadow width (solid squares) of the 7 micron capillary increases as the distance of the vessel from the photoreceptor increases. Second, and more importantly, notice the width of the shadow having a uniform illuminance profile (open squares) at first decreases to zero and then increases. Like FIG. 6A, the decreasing portion of this function reflects the gradual movement of the umbra to a position anterior to the photoreceptor. Further increases in vessel distances (greater than approximately 140 microns) produce increases in the width of the central uniform section of the illuminance profile. As the width of the uniform section of the illuminance profile increases, the illuminance of this section increases and lowers shadow contrast (FIG. 7B). The width of the ramping portion of the shadow (open circles, FIG. 7A) at first increases as the uniform portion decreases to zero and then remains essentially constant as the capillary to photoreceptor distance continues to increase. While this analysis demonstrates that total shadow width for the smallest capillary is always considerably bigger (>10 microns) than a photoreceptor (2 microns), it does not indicate whether or not there is sufficient total contrast or if the spacing of shadows is adequate for perception.

2. Contrast of the Shadows

As illustrated in FIG. 7B, the relative shadow contrast is affected by vessel size and position. As can be seen, the use of a small 1 mm diameter source ensures a full contrast shadow for all but the smallest vessels positioned near the ILM. Vessels larger than 15 microns will always have a portion of the umbra in the plane of the photoreceptors. The lowest contrast expected for 7 micron capillaries positioned 300 microns from the entrance aperture of the photoreceptors (worst case situation) using a 1 mm source, is approximately 50% of the maximum. Now the question becomes, is this contrast reduction sufficient to render the shadow of these small capillaries invisible? To answer this question the actual contrast of the shadow must be determined.

Bird and Weale (7) have discussed this issue and, using estimates of hemoglobin absorption for white light in small capillaries to be 40% (transmission 60%), they calculate log I/I to be −1.6 (or a contrast of 2.5%). Using the same estimate of hemoglobin transmission, we calculate a maximum shadow contrast of 40% [(1-%0.6)/(1)]. Thus a 7 micron capillary 300 microns in front of the photoreceptor entrance aperture experiencing a 50% reduction in contrast should have a contrast of approximately 20%. Larger sources (greater than 1 mm) will further decrease the shadow contrast of the small 7 micron vessels (FIG. 6B) and expand the range of vessel widths affected with a contrast loss. Smaller sources (less than 1 mm) will increase the contrast of the smaller vessels and decrease the range of vessels widths affected with a contrast loss. This analysis helps to explain why trans-scleral illumination with a source such as a penlight or illuminator (which presumably becomes even larger due to scatter within the sclera) does not provide an easily visible entoptic view of the foveal capillaries.

Figure 8:
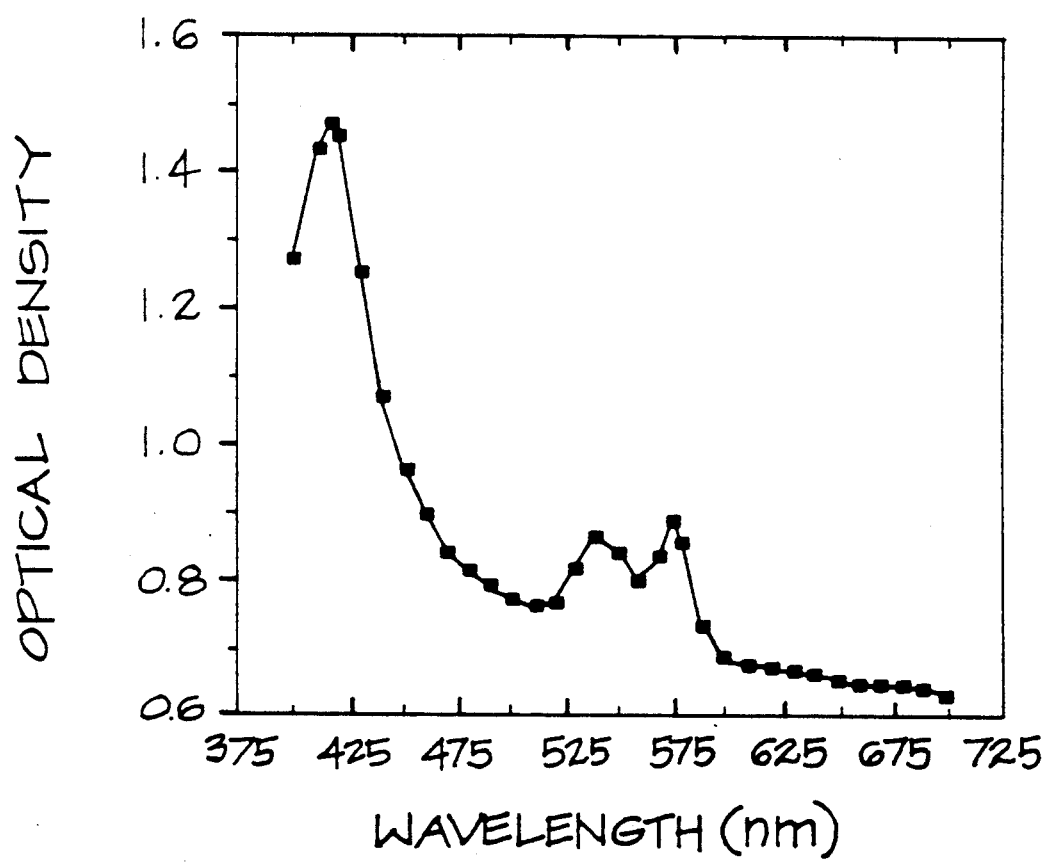
FIG. 8 shows the optical density of whole blood (subject RAA) diluted 500 times through a pathlength of 1 cm as a function of wavelength.

The contrast of the vascular shadows can be increased further for any sized source by limiting the spectral output of the source to the absorption peak for blood and, in particular, hemoglobin. FIG. 8 illustrates the optical density for a 1 cm optical pathlength of one of the inventor's blood (RAA) diluted 500 times as a function of wavelength. As can be seen from this figure, blood has its maximum optical density (absorption) in the visible spectrum at 415 nm which corresponds with the maximum density for oxyhemoglobin. Given the wavelength of maximum absorption for deoxyhemoglobin is 430, limiting the spectral output of 1 mm diameter source imaged in the plane of the eye's entrance pupil to a band between 415 and 430 will increase the shadow contrast of a 7 mm capillary from 20% to approximately 45% [i.e., 1.47 (optical density of whole blood diluted 500 times at 415 nanometers)+2.7 (correction for 500 times blood dilution)−3.15 (correction for 1 cm measurement thickness to 7 micron capillary thickness)=1.02; as a result, transmission through the capillary will be approximately 9.55% of the incident light creating a contrast of (1-0.0955) /(1)=90.45% in the umbra (which lies in front of photoreceptors in the case of the 7 micron capillary) and 45.23% in the plane of the photoreceptors].

While a short-wavelength narrow-band source (415 to 430 nm) theoretically provides the best retinal contrast, practically, as a result of the lower sensitivity of the middle and long wavelength sensitive cone mechanisms to short wavelength light the reduced spatial resolution of the short wavelength sensitive cone mechanism, the low output of tungsten light sources at short wavelengths and the loss of contrast sensitivity with decreasing retinal illuminance, it is better to use fairly broad spectrum source of slightly longer wavelength (after trial and error, it has been found that a 3M color filter part #47 with peak transmittance at 470 nm half band pass +/− 60 nm worked well.).

3. Shadow Spacing

Periodic grating patterns having a contrast of 40% are easily visible at photopic light levels for spatial frequencies up to 30 cycles/degree. Detailed photographs of latex-filled retinal vessels around the fovea (of Macaque) show capillaries every 28 microns (or 5.7 minutes of arc) or approximately 10 vessels per degree. Periodic grating patterns of 10 cycles/degree can be detected with contrasts of approximately 1% at the fovea but they become invisible at 5 degrees eccentric to the fovea. To the extent grating data can be generalized to the periodic but irregular shadow pattern of the retinal vasculature, the finest detail of the smallest macular capillaries should be easily visible. This is, of course, assuming that image stabilization is appropriately broken.

4. Shadow Movement

Sharpe (12) carefully analyzed the parameters of shadow movement necessary for entoptic perception. He noted: (1) For perception of the fine capillaries, the shadows must move smoothly from one photoreceptor to the next; (2) Since the maximum movement of any shadow is provided by source movement perpendicular to the orientation of the vessel of interest, perception of the whole vascular bed is best perceived by a random or circular motion of the source; (3) Despite optimization, the percept of the shadows fade within approximately 60 seconds presumably due to adaptation of pattern detectors.

Previous evidence suggests for longest duration of the entoptic percept the vascular shadows should drift at approximately 150 min of arc/sec and drift over a distance of approximately 40 min of arc. This finding was verified experimentally by changing the diameter of the circular path our source followed in 1 mm steps and adjusting the velocity of the rotation for each path diameter for optimal vessel perception. This verification process revealed that little, if any, improvement in perception was obtained with a source rotation diameter greater than 4 mm and an associated rotation frequency of 3.5 Hz. Interestingly, for vessels located 300 microns from the photoreceptor entrance aperture this stimulus configuration caused each point of the vascular shadow to move in a circle over a distance of approximately 38 min. of arc at a velocity of approximately 134 min of arc/sec, a finding consistent with Sharpe's original work (12). However, the distance and velocity over which the vascular shadows move vary with vessel location.

Figure 9A:
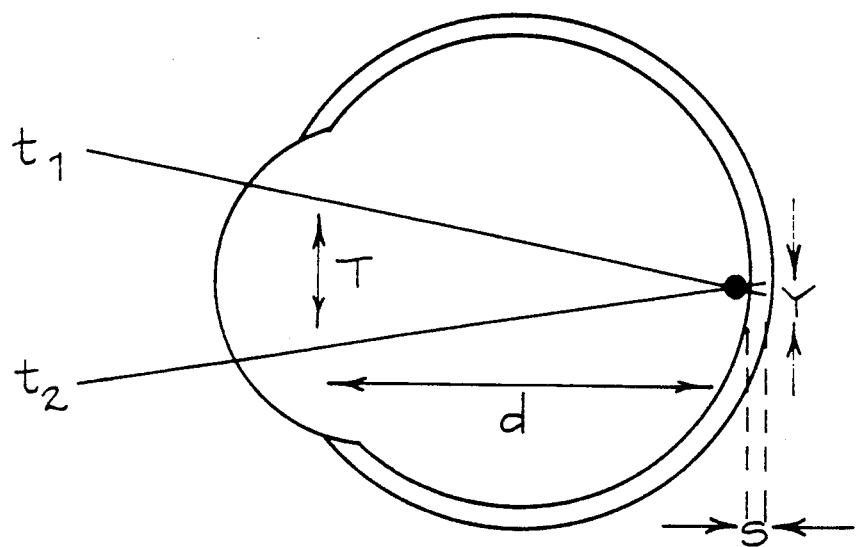
FIG. 9, panel A shows vessel shadow movement y induced by movement T of a small source in the plane of the eye's exit pupil; panel B exaggerates the scale to illustrate the effect.
Figure 9B:
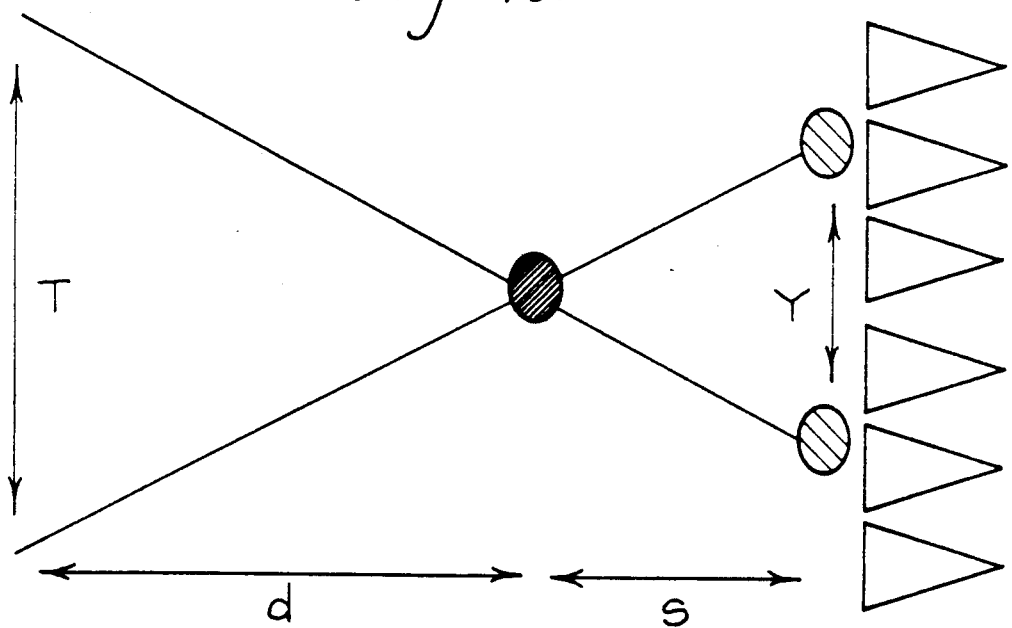

FIG. 9A illustrates the chief ray of the source as it travels its circular path at two different points in time ($t_1$ and $t_2$) 180 degrees apart. Notice that a vessel at a distance s from the entrance aperture of the photoreceptors has a shadow which is displaced by a maximum distance of y when the source is travelling in a circle of diameter T in the entrance pupil of the eye. The geometry of this configuration is more clearly illustrated in FIG. 9B.

Figure 10:
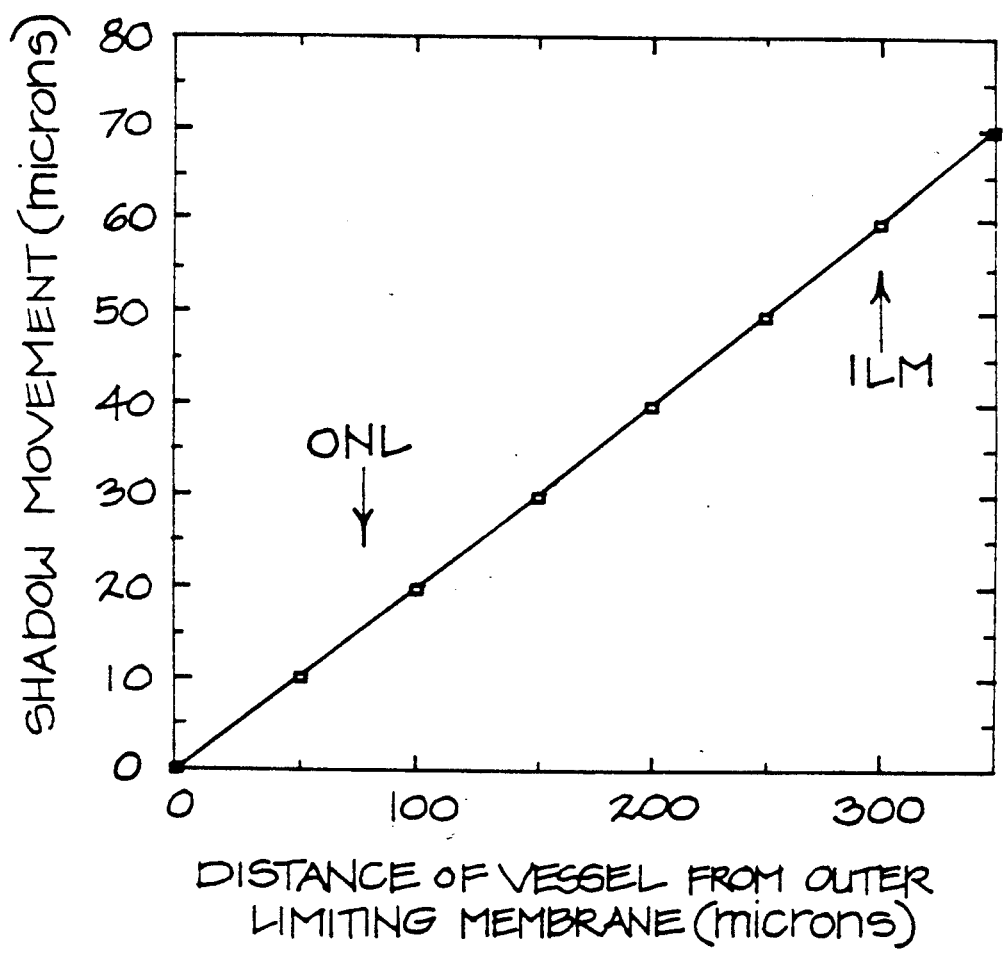
FIG. 10, illustrates maximum shadow movement perpendicular to the long axis of the vessel induced by a small source rotating along a circular 4 mm diameter path in the plane of the eye's entrance pupil as a function of vessel distance from the photoreceptor entrance aperture.
Figure 11:
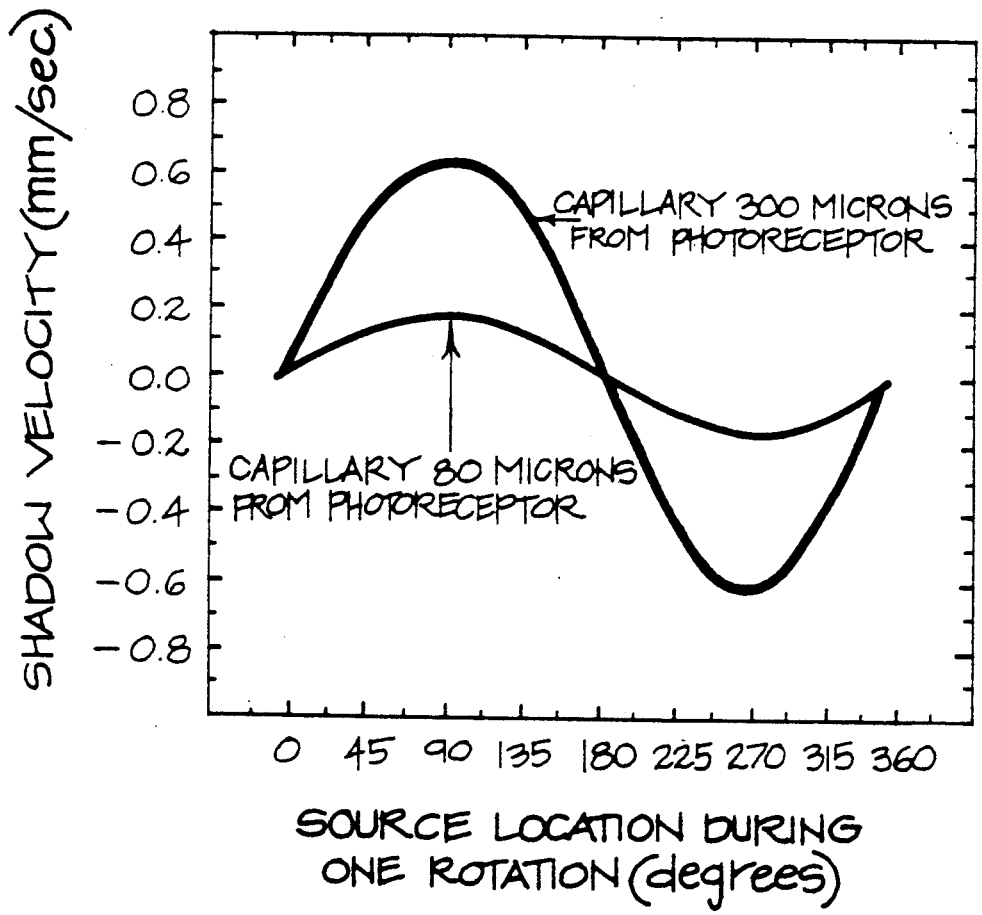
FIG. 11 shows shadow velocity perpendicular to the long axis of the vessel at the plane of the entrance aperture of the photoreceptors resulting from a small source rotating along a circular 4 mm diameter path in the plane of the eye's pupil as a function of source location.

FIG. 10 illustrates the maximum shadow movement perpendicular to the vessel's long axis as a function of the distance of the vessel from the photoreceptors. FIG. 11 displays the variation in shadow velocity perpendicular to the long axis of the capillary as a function of source location during one complete rotation of the source in the eye's entrance pupil. Calculations for FIGS. 10 and 11 were made using a chief ray moving in a circular 4 mm diameter path in the plane of the eye's entrance pupil. As can be seen in these figures, the shadow of a vessel located in the ONL moves a distance perpendicular to the long axis of the capillary of approximately 59 microns with a velocity varying between 0 and 653 microns/second (0 and 134 min of arc/sec) while a vessel located at the ILM moves approximately 16 microns at a velocity varying between 0 and 171 microns/second (0 an 35 min of arc/sec). More importantly, this stimulus configuration moves any point on the shadow over approximately 35 to 134 photoreceptors per second depending on vessel location. This experimentally determined rotation speed of the source and resulting shadow drift rat is consistent with data from image stabilization experiments that report optimal drift velocities of 15 min of arc/sec for detection of a 10 cycle/degree grating.

The operating principles of the vascular entoptoscope, which provides a view of the retinal vasculature, can be combined with the operating principles of the Blue Field Entoptoscope, (see U.S. Pat. Nos. 4,425,924 and 4,476,878 to Riva et al., incorporated by reference herein for the method and apparatus therein disclosed) which provides a view of the white blood cells. The end product of such a combination will provide a view of the white blood cells moving within the vasculature. This combined unit will, depending on which subunit is turned on, provide a view of: (1) The retinal vasculature by itself; (2) the movement of the white blood cells by itself; or (3) the movement of the white blood cells within the retinal vasculature.

The following Examples are presented to describe the best mode of the present invention and are not meant to limit the invention numbers otherwise specified in the claims appended hereto.

EXAMPLE 1

A. Vascular Entoptoscope Sub-System: The components of the Vascular Entoptoscope are illustrated in FIG. 12.

Source S, a 1 mm pinhole back-illuminated by light from a fiber-optic passing through a blue filter (peak transmittance at 470 nm with a 50 nm ½ band pass), rotates at a speed of 3.5 Hz in a circular path 2 mm from, and concentric with, the optical axis of the instrument. Light from S is first collimated by lens $L_1$, and then imaged into the plane of the subject's pupil with unit magnification by lens $L_2$. An iris diaphragm (aperture A) imaged at optical infinity by $L_2$-serves as the field stop for the eye apparatus system.

A second channel provides the subject a view of two dim point sources ($PS_1$ and $PS_2$) optically conjugate with aperture A via beam splitter $B_1$. Point source $PS_1$ is attached to a motorized X-Y positioning plate and serves as a guidelight for marking positions of interest within the field of view. Point source $PS_2$ serves as a stationary fixation point centered on the optical axis of the apparatus. The subject controls the position of $PS_1$ with a joystick, and can thereby locate, with respect to the point of fixation, any point on the capillary loop defining the FAZ. A variable voltage signal reflecting the location of moveable point source $PS_1$ is sent from the X-Y position plate to an X-Y plotter for hard-copy documentation of the border of the FAZ. Depending on user preferences and goals, a digital sensor or antilog to digital converter sending its signal to a computer for on screen display may be the preferred readout device.

Figure 12:
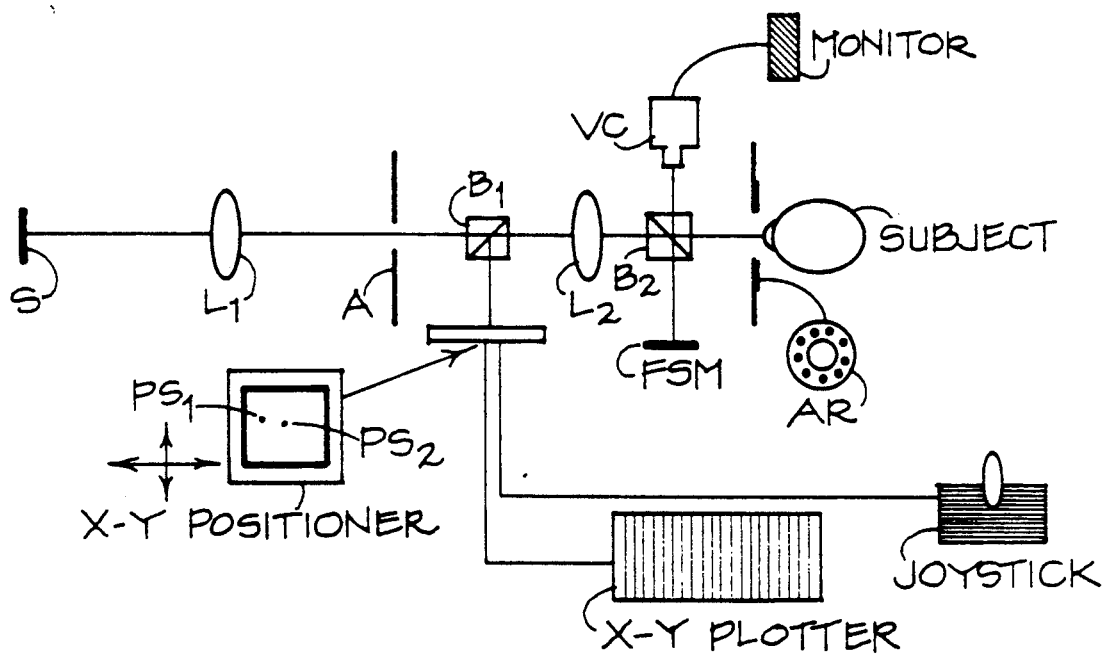
FIG. 12 is a schematic representation of the Instrument. S: source, a rotating 1 mm pinhole for the Vascular Entoptoscope sub-component and a stationary centered pinhole for the Blue Field Entoptoscope sub-component; $L_1$: collimating lens; A: variable iris diaphragm; $B_1$: beam splitter; $L_2$: Maxwellian view lens; $B_2$: beam splitter; VC: video camera; AR: alignment ring; $PS_{1\&2}$: point sources.

Alignment of the subject's pupil to the optical axis of the apparatus and stabilization of the subject's head is obtained with a chin and forehead rest (or bite bar) mobile in three planes (not illustrated in FIG. 12). To insure the subject is properly aligned to the apparatus, a third channel provides a closed-circuit video view of the pupil entry location of the rotating beam and the corneal reflection of alignment ring AR (a circle of infra-red LED's concentric with the optical axis of the apparatus). The video view of the rotating beam is obtained by deflecting some of the beam from source S at beam splitter $B_2$ onto a front surface mirror (FSM, optically conjugate with the subject's entrance pupil) and back through beam splitter $B_2$ into the video camera (VC). The video view of alignment ring AR is obtained by reflection off the subject's cornea back into the apparatus and reflection at beam splitter $B_2$ into the video camera. By continually observing the information on the monitor, the experimenter can maintain subject/apparatus alignment by adjusting the position of the chin rest.

Figure 13:
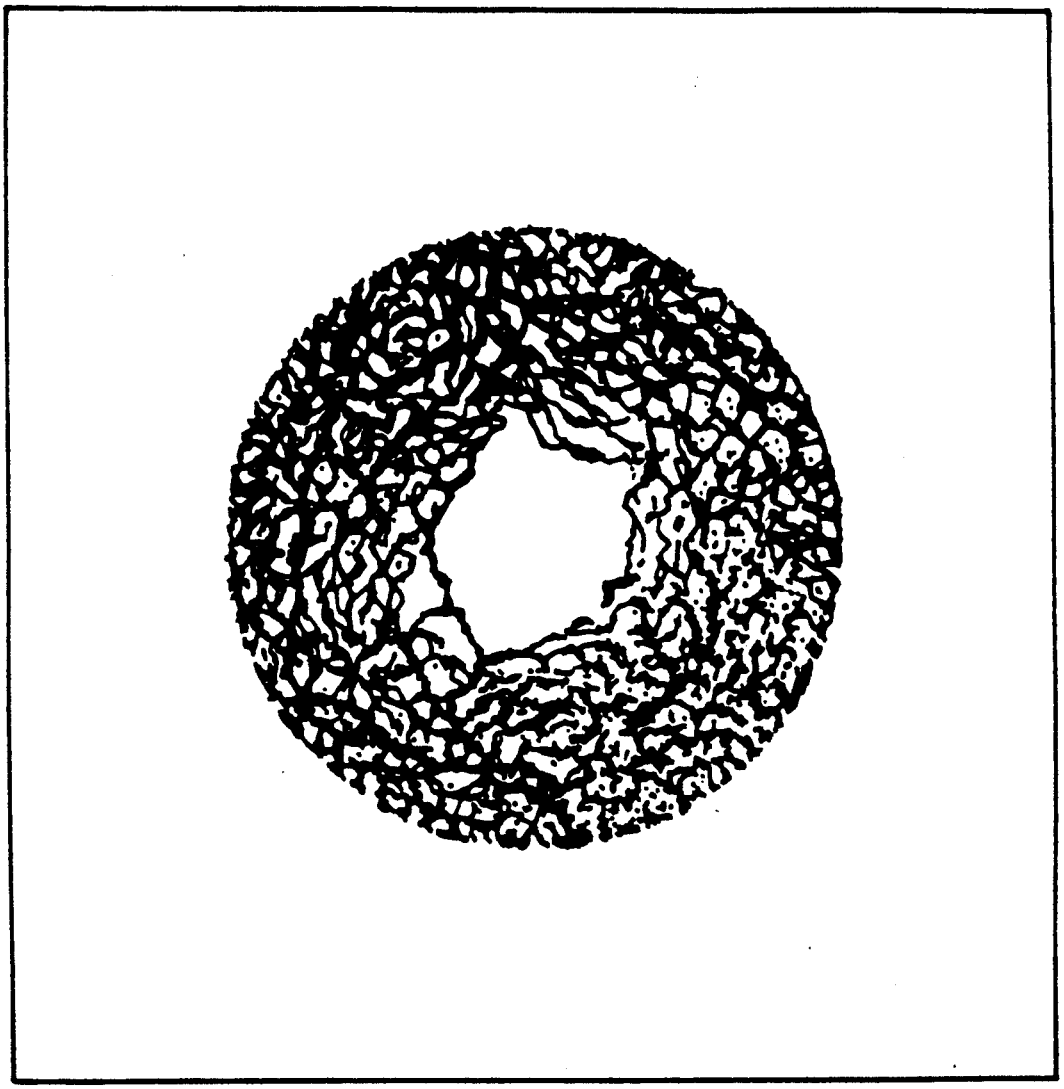
FIG. 13 shows a simulation of entoptic percept of the macular area retinal vasculature.
Figure 14A:
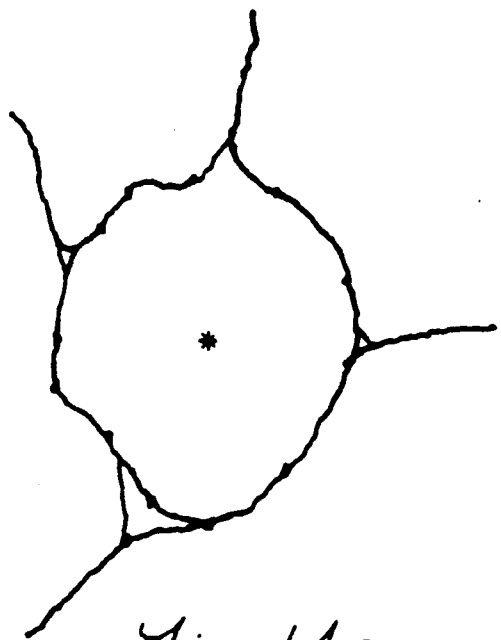
FIG. 14 describes four FAZ tracings. Panel A: Classic FAZ tracing with centered fixation point; Panel B: FAZ tracing showing a typical eccentric location for the retinal point of fixation; Panel C: FAZ tracing showing the largest eccentric distance between the geographic center of the FAZ and the retinal point of fixation; Panel D: Tracing showing no FAZ and retinal capillaries near the retinal point of fixation. *=center of fixation; +=geographic center of FAZ.
Figure 14B:
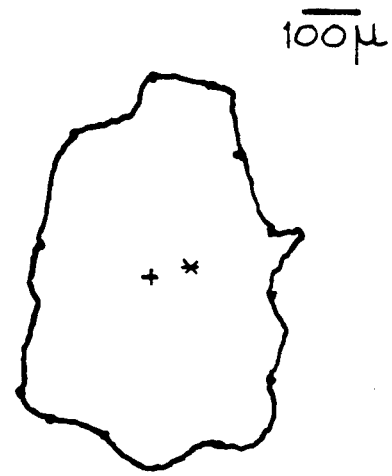
Figure 14C:
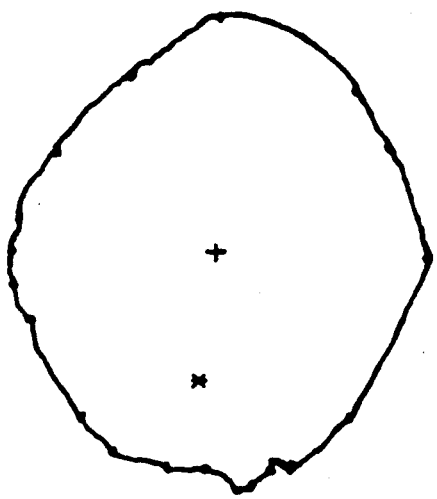
Figure 14D:
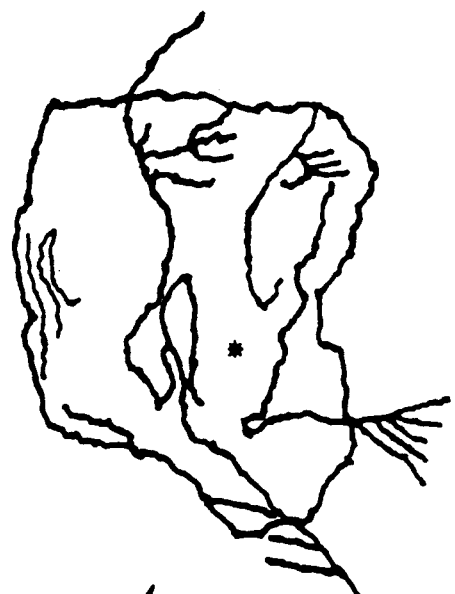

Any channel can be optically folded by appropriate mirrors and other powered lenses (obeying the principles outlined above) can be used without violating the operating principles of the instrument. A realistic simulation of the user's entoptic percept (less the view of the point sources $PS_1$ and $PS_2$) is provided in FIG. 13.

B. Blue Field Entoptoscope Sub-System: To see the white blood cells entoptically, as opposed to the vessels, all that is necessary is to stop the rotation of the rotating pinhole. The perception of the white blood cells can be enhanced by shifting the wavelength of the source to shorter wavelengths (approximately 435 nm). However, given that the complete system is designed to allow the entoptic view of the vessels, the entoptic view of the white blood cells or both the entoptic view of the vessels and the white cells simultaneously, it is best to add a centered (non-rotating) source in the same plane as the source S of FIG. 13. Thus, the centered source is on by itself when viewing the movement of the white blood cells alone and the eccentric rotating source is on by itself when viewing the retinal vasculature alone.

C. Combined viewing of both the movement of the white blood cells and the retinal vasculature is achieved by having both the rotating source and the centered source on simultaneously and adjusting the intensities of both for optimal perception of both entoptic effects.

EXAMPLE 2

Normal Patients

The Vascular Entoptoscope subsystem has been used to test normal and diabetic eyes. All subjects easily saw the Purkinje image of their retinal capillaries. Ten of the 14 normal subjects tested to date graphed details of the shadow of their FAZ in both eyes, and 2 (due to personal time constraints), in only one eye. Another subject observed a traditional FAZ in one eye, but saw capillaries running through what should have been the FAZ in the other; and one subject saw capillaries running through the fixation point in both eyes. FIG. 14 depicts a sample of the variety of FAZ tracings obtained. Panel A displays the tracing of one of only 3 eyes with a retinal point of fixation located in the geographic center of the FAZ as classically described anatomically. Panel B displays a tracing from an eye with the retinal point of fixation located a typical distance from the geographic center of the FAZ; whereas, Panel C displays the tracing of the subject with the largest distance ($189\mu$) between the retinal point of fixation and the geographic center of the FAZ. Panel D displays the tracing of one of 3 eyes with vessels in the retinal area more commonly occupied by the FAZ. Even by casual observation, it becomes clear that the FAZ boundaries are not always concentric with the fixation point (Panel B and C).

Figure 15:
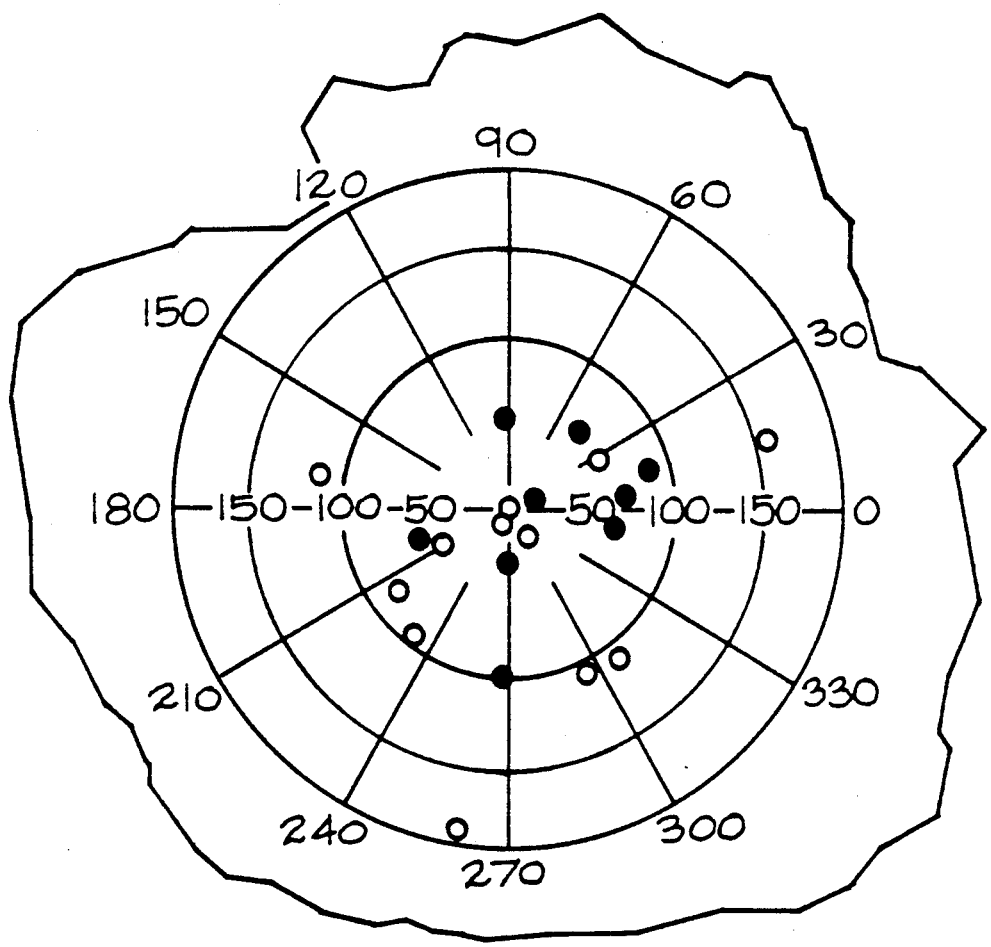
FIG. 15 illustrates location of the retinal point of fixation from the geographic center of the FAZ tracing for each eye tested. Left eyes open circles, right eyes closed circles. Irregular circular pattern represents a typical FAZ border. Units: Angles in degrees, distances in microns.

All 23 eyes with FAZs had retinal fixation points located within the FAZ. However, only three eyes from three different subjects had their retinal points of fixation located at the geographic center of the FAZ. Vectors defining the distance from the geographic center of the FAZ to the subject's fixation point and the direction of deviation (with 0° being horizontal to the right) were determined for each FAZ tracing. These distances were then converted to retinal distances using the Gullstrand reduced model eye with a nodal-point to retina distance of 16.67 mm after compensating for the optical magnification factor of the Maxwellian view optical system and the gain of the X-Y plotter. FIG. 15 uses a polar coordinate system to illustrate the location of the retinal point of fixation relative to geographic center of the FAZ for each eye tested. Note that while the data as a whole tends to cluster near the origin (i.e., the retinal point used for fixation tended to be nearer the center of the FAZ as opposed to the edge of the FAZ) the distribution of directions of deviation appear random. The largest deviation of the retinal point of fixation from the geographic center of the FAZ was $189\mu$. The average deviation from the geographic center across all subjects is $66.50\mu$. There was no tendency for the eccentricity of the retinal point of fixation to increase with increasing FAZ diameter.

This data indicate that the retinal point of fixation deviates from the geographic center of the FAZ by about $65\mu$ (SD$+/-$ $50\mu$) with a range of 0 to $190\mu$. These findings suggest that laser burns centered on retinal points less than $300\mu$ from the geographic center of the FAZ run a significantly higher risk of falling directly on or nearer to the retinal point of fixation than intended. Further, the risk of burning the point of fixation can markedly increase as burns are placed closer to the geographic center of the FAZ. The implications of this finding are profound and find support in current literature,.

Figure 16:
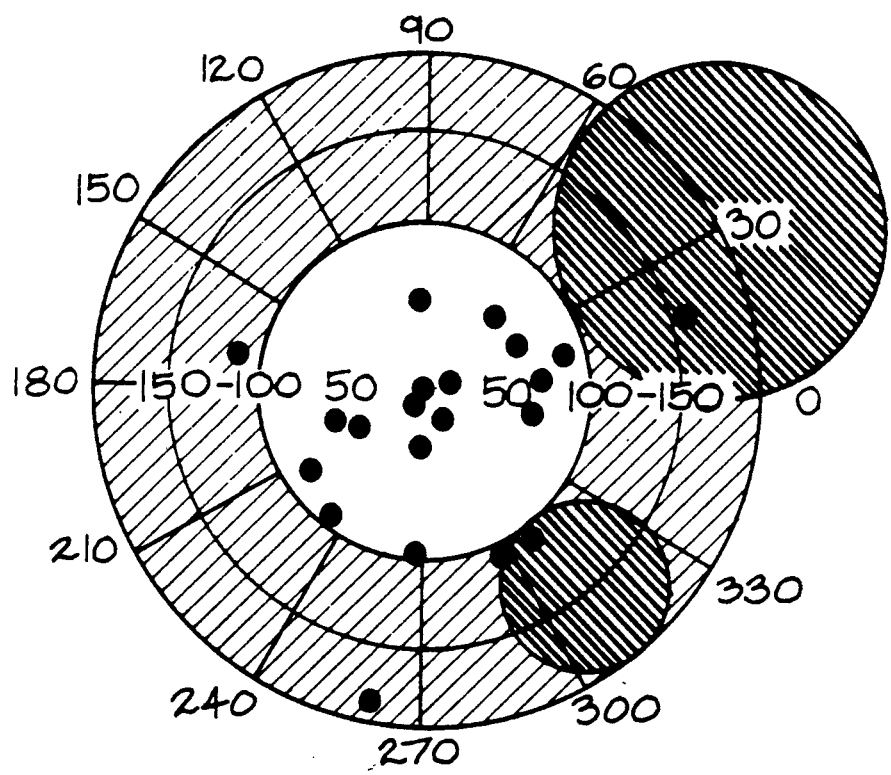
FIG. 16 demonstrates location of the retinal point of fixation (solid dots) from the geographic center of the FAZ tracing for each eye tested. Lightly shaded area represents the area at risk of damage from a single $200\mu$ or $100\mu$ laser burn (darkly shaded circles) placed to overlap a lesion $200\mu$ from the center of the FAZ by $100\mu$.

To illustrate, assume that, as in recent clinical trials, 1-4 retinal lesions up to $200\mu$ from the FAZ center are treated with burns which overlap the lesion by up to $100+\mu$. Further, grant that the data present herein form a representative sample of the population for the location of the retinal point of fixation with respect to the geographic center of the FAZ (data points, FIG. 15). With these assumptions, 6 of 24 eyes (25%) have retinal points of fixation which are potentially vulnerable to being burned (FIG. 16, lightly shaded area). However, since photocoagulation treatment is generally limited to or slightly overlaps the area of frank pathology (e.g., neovascular membrane, histo-spot, etc.), it is likely that a series of burns will be placed only within the sector of the macular area containing the site of the lesion (FIG. 16 darkly shaded circles schematically show both a 200 and $100\mu$ burn). Under these criteria and if the treatment sector of the macular area is limited to 90°, it is likely that for any one particular series of burns one or two eyes out of our sample of 24 (4 to 8%) would have their retinal point of fixation adversely effected by photocoagulation therapy.

The obvious question arises as to what percentage of treatment failures (loss of 6 lines of visual acuity or more at first follow-up) can be accounted for by variations in the location of the point of fixation with respect to the geographic center of the FAZ. While this question cannot be definitively answered with the data collected to date, it is interesting to note that with argon treatment it has been reported that 9% of eyes treated for neovascular maculopathy (13) 9% of the eyes treated for macular area ocular histoplasmosis (14) and 10% of those eyes treated for macular area idiopathic neovascularization (15) lost 6 or more lines of visual acuity at first follow-up despite "successful" treatment of the pathology. Further, this order of magnitude of initial follow-up failure is not unique to argon treatment.

Studies using krypton therapy for histoplasmosis have reported a similar percentage of patients (8%) with a 6 line loss in visual acuity at first follow-up (16). The argument is further fueled by the fact that the best predictor of visual acuity loss despite adequate therapy is treatment proximity to the center of the FAZ (17). That is when analysis is limited to eyes with lesions within $375\mu$ of the FAZ center between 8 and 33% of the eyes successfully treated lost 6 lines or more at first follow-up depending on the particular study. While this could be accounted for by assuming the lesions within $375\mu$ are more likely to effect the retinal point of fixation, the data presented herein suggest another possibility. Given the uncertainties of thermal spread, dose specification, actual spot size in the plane of the retina, variation in pigment absorption and accuracy of burn placement with respect to desired location, the speculative estimate of 4 to 8% may indeed be an underestimate of the number of retinal fixation points at risk. Simply allowing for $50\mu$ of uncertainty would raise the number of retinal fixation points at risk from 4 to 8% up to 16 to 20%. To the extent this analysis is correct, it suggests that therapeutic failures at first visit for eyes with retinal lesions between 200 and $375\mu$ could be reduced by as much as 20% by using the actual retinal point of fixation as a reference as opposed to the geographic center of the FAZ.

In summary, the normal patient data collected using the Vascular Entoptoscope of the present invention indicate the retinal point of fixation is not always centered within the FAZ. Further, the deviations of the retinal point of fixation from the center of the FAZ can be large enough to jeopardize the retinal point of fixation during foveal area laser photocoagulation therapy which avoids the center of the FAZ as opposed to locating and avoiding the retinal point of fixation.

EXAMPLE 3

Abnormal Patients

To date the Vascular Entoptoscope has been used to test approximately 25 diabetic patients to determine if they could detect their own retinal vascular abnormalities (i.e., microaneurysm in particular). All individuals tested could see their own defects. This raised the distinct possibility of the methods revealed here being used to develop an inexpensive take-home device to be used for early detection.

EXAMPLE 4
Combined System

While a working model of the instrument that combines both a Blue Field Entoptoscope (which provides a view of the white blood cells as they move through the macular area retinal capillaries) and a Vascular Entoptoscope is not yet available, the results to date show that both systems independently work extremely well. Further, little if any difficulty is anticipated in combining the two units into one and providing the viewer one of three options:

(1) An entoptic view of their own retinal vasculature;
(2) An entoptic view of the movement of their own white blood cells; and
(3) A view of their own white blood cells as they travel through the retinal capillaries.

While each view has its own distinct benefits which are important by themselves, the simultaneous view has several unique advantages which include:

(1) Allowing the viewer to determine the rate of blood flow through any capillary of interest;
(2) Allowing the viewer to examine vascular irregularities (such as microaneurysms) and how they alter blood flow; and
(3) Determining whether or not a particular capillary is patent.

The following references in pertinent part are incorporated herein for the reasons cited above.

References

1. Laatikainen K. and Larinkari J: Capillary-free area of the fovea with advancing age. Invest. Ophthalmol Vis Sci 16:1154–1157, 1977.
2. Bresnick GH, Condit R, Syrjala S, Palta M, et al: Abnormalities of the foveal avascular zone in diabetic retinopathy. Arch. Ophthalmol 102:1286–1293, 1984.
3. Bligard E, de Venecia G, Wallow I, et al: Aging changes of the parafoveolar vasculature: a trypsin digest study. Invest Ophthalmol Vis Sci Suppl 22:8, 1982.
4. Weale RA: Why does the human retina possess a fovea? Nature 212:255–256, 1966.
5. Dartnall HJA and Thomson LC: Retinal oxygen supply and macular pigmentation, Nature 164:876, 1949.
6. Purkinje JE: In Beobachtungen und Versuche zur Physiologie der Sinne. J. Calve, Prague, 1819.
7. Bird AC and Weale RA: On the retinal vasculature of the human fovea. Exp Eye Res 19:409–417, 1974.
8. Yeung J, Crock G, Billson F, et al: New observation on retinal microcirculation at the posterior pole in man. Trans Fourth Asia-Pacific Congress Ophthal 25:155–161, 1973.
9. Kluxen G and Wilden E: An entoptic test in diabetic patients. Diabetes Care 10:800–801, 1987.
10. Helmholtz H: Treatise on Physiological Optics, Southall JPC, editor. New York, Dover Publications, Inc., 1962, Vol I pp. 217–218.
11. Shimizu K and Ujiie K: In Structure of ocular vessels. New York, Igaku-Shoin, 1978.
12. Sharpe CR: A Fresh Approach to Stabilized Retinal Images. Part II. J Physiol 217:9–10, 1971.
13. Macular Photocoagulation Study Group: Argon laser photocoagulation for neovascular maculopathy: Three year results from randomized clinical trials. Arch. Ophthalmol. 104:694–701, 1986.
14. Macular Photocoagulation Study Group: Argon laser photocoagulation for ocular histoplasmosis: Results of a randomized clinical trial. Arch Ophthalmol 101:1347–1357, 1983.
15. Macular Photocoagulation Study Group: Argon laser photocoagulation for idiopathic neovascularization: Results of a randomized clinical trial. Arch Ophthalmol 101:1358–1361, 1983.
16. Macular photocoagulation Study Group: Krypton laser photocoagulation for neovascular lesions of ocular histoplasmosis: Results of a randomized clinical trial. Arch Ophthalmol 105:1499–1507, 1987.
17. Han DP, Folk JC, and Bratton AR: Visual loss after successful photocoagulation of choroidal neovascularization. Ophthalmol 95:1380–1384, 1988.

What is claimed is:

1. An apparatus for entoptically perceiving and mapping the foveal area vasculature of the retina of a human subject's eye under examination, the apparatus comprising:
   (a) a means to establish and maintain translational and rotational alignment of said eye with said apparatus;
   (b) a main light source which is imaged in or near the eye's entrance pupil plane and a means of moving said main light source or said image along a path in space, said main light source being of variable intensity and shape;
   (c) a means of directing said main light image into said eye's entrance pupil, resulting in an angle of illumination of said eye's retina changing with time;
   (d) a means to image an aperture at optical infinity or other plane of interest to correct for any refractive error as an optical field stop for said apparatus, said aperture being of variable size and shape;
   (e) a fixation light source and a means to form a fixation light image on the retina of said eye, said fixation light source being of variable intensity;
   (f) a tracking light source and a means to form an image of tracking light from said source on the retina of the eye, said tracking light source being of variable intensity;
   (g) a means of moving said tracking light retinal image with respect to said fixation light retinal image;
   (h) a means of transducing movement of said tracking light retinal image to yield coordinates of its present location on said eye's retina with respect to said fixation light retinal image;
   (i) a means of compiling or displaying said coordinates of said tracking light retinal image movement, said compilation or display comprising a map of said tracking light retinal image positions with respect to said fixation light retinal image; and
   (j) a means to detect and indicate magnitude and direction of translation of said eye with respect to said apparatus.

2. The apparatus of claim 1 wherein the means to establish and maintain rotational alignment is a bite bar for the subject to orally embrace or a chin and forehead rest.

3. The apparatus of claim 1 wherein said main light image path is circular, about 2 to 6 mm in diameter and about centered in the eye's pupil.

4. The apparatus of claim 1 wherein said main light image path is circular, 4 mm in diameter and about centered in the eye's pupil.

5. The apparatus of claim 1 wherein said main light path is circular, being retraced at the rate of about 0.5 to 10 Hz.

6. The apparatus of claim 1 wherein said main light path is circular, being retraced at the rate of about 3.5 Hz.

7. The apparatus of claim 1 wherein said aperture is that of an adjustable iris diaphragm.

8. The apparatus of claim 1 wherein said eye's area of retinal illumination comprises a circle and said fixation light retinal image is within said circle.

9. The apparatus of claim 1 wherein said eye's area of retinal illumination comprises a circle and said fixation light retinal image is centered within said circle.

10. The apparatus of claim 1 wherein said main light source has a peak wavelength of about 430 to 555 nm and a half band pass of about +/− 60 nm.

11. The apparatus of claim 1 wherein said main light source has a peak wavelength of about 470 nm and a half band pass of +/− about 60 nm.

12. The apparatus of claim 1 wherein said main light source image is circular with a diameter of about 0.5 to 3 mm.

13. The apparatus of claim 1 wherein said main light source image is circular with a diameter of about 1.0 mm or less.

14. The apparatus of claim 1 wherein said main light source is imaged in or near said eye's entrance pupil plane.

15. The apparatus of claim 1 wherein said main light source is imaged in or near said eye's anterior focal plane.

16. The apparatus of claim 1 wherein said main light source image is diffuse and of uniform intensity.

17. The apparatus of claim 1, where in step (j) said indication of magnitude and direction of translation of said eye with respect to said apparatus is visible.

18. The apparatus of claim 1, where in step (j) said indication of magnitude and direction of translation of said eye with respect to said apparatus is sensed by an external operator.

19. The apparatus of claim 1 where in step (j) said indication of magnitude and direction of translation of said eye with respect to said apparatus is sensed by a sensor and monitored by a computer.

20. The apparatus of claim 1 wherein said tracking light retinal image coordinates of steps (h) and (i) are corrected manually for retinal image translation caused by any translation of said eye with respect to said apparatus.

21. The apparatus of claim 1 wherein said tracking light retinal image coordinates of steps (h) and (i) are corrected by automatic computation for retinal image translation caused by translation of said eye with respect to said apparatus.

22. The apparatus of claim 1 wherein said tracking light retinal image coordinates in step (i) are calibrated in units of length measured on said retinal surface.

23. The apparatus of claim 1 wherein said tracking light retinal image coordinates in step (i) are calibrated in units of angular subtense.

24. The apparatus of claim 1 wherein said means of moving said tracking light retinal image is a joy stick or similar x-y manual controller.

25. A method for entoptically perceiving and mapping the foveal area vasculature in the retina of the eye of a human subject under examination with respect to the retinal point of fixation of said eye, the method comprising:
  (a) optically directing a main light source image within said eye's entrance pupil to illuminate a portion of said eye's retina defined by a field stop, said image being of variable intensity;
  (b) causing said main light source image to move along a main light path in space, said main light path in space resulting in said eye's angle of retinal illumination changing with time;
  (c) optically directing a fixation light source on said eye's retina and forming thereon a fixation light retinal image, said fixation light source image being of variable intensity;
  (d) having said subject visually fixate on said fixation light source image;
  (e) having said subject report descriptions of entoptically perceived vascular features of interest near the foveal area of said eye;
  (f) optically directing a tracking light source on said eye's retina and forming thereon a tracking light retinal image, said tracking light source image being variable in intensity and movable over said eye's retinal surface with respect to said fixation retinal image through a tracking light controller operated by said subject;
  (g) causing said fixation light, and tracking light source images to be viewed by said eye through an optical field stop aperture illuminated by the main light, said aperture being imaged at infinity or other plane of interest;
  (h) scaling outputs of said tracking light controller to correspond to distances and angles measured on said eye's retinal surface;
  (i) having said subject move said tracking light retinal image along or around said entoptically perceived vascular features of interest while said subject maintains constant translational and rotational alignment of said eye with said fixation light retinal image;
  (j) using said scaled outputs of said tracking light controller to create position reports of said entoptically perceived vascular features of interest on said eye's retina;
  (k) combining said position reports with said descriptions of said entoptically perceived vascular features of interest to create a retinal vascular map;
  (l) having said subject adjust said intensities of said main, fixation and tracking light sources for best entoptic visualization;
  (m) having said subject adjust complete rotation frequency and thus velocity of the main light source image;
  (n) observing said eye to detect misalignment with said fixation light retinal image due to any combination of translation or rotation of said eye;
  (o) determining corrections required to said position reports resulting from said misalignment of said eye with respect to said fixation light retinal image; and
  (p) applying said corrections to said position reports.

26. The method of claim 25 wherein said main light path in space is circular.

27. The method of claim 25 wherein said main light path in image space is circular, 2 to 6 mm in diameter, and about centered in the eye's pupil.

28. The method of claim 25 wherein said main light path in image space is about 4 mm in diameter and about centered in the eye's pupil.

29. The method of claim 25 wherein said main light path in space is circular, being retraced at the rate of about 0.5 to 10 Hz.

30. The method of claim 25 wherein said main light path in space is circular, being retraced at the rate of about 3.5 Hz.

31. The method of claim 25 wherein said field stop aperture is an adjustable iris diaphragm.

32. The method of claim 25 wherein said eye's area of retinal illumination comprises a circle and said fixation light retinal image is within said circle.

33. The method of claim 25 wherein said eye's area of retinal illumination comprises a circle and said fixation light retinal image is centered within said circle.

34. The method of claim 25 wherein said main light source image has a peak wavelength of about 430 to 555 nm and a half band pass of about +/− 60 nm.

35. The method of claim 25 wherein said main light source image has a peak wavelength of about 470 nm and a half band pass of about 60 nm.

36. The method of claim 25 wherein said main light source image is circular with a diameter of about 0.5 to 3 mm.

37. The method of claim 25 wherein said main light source image is circular with a diameter of about 1.0 mm or less.

38. The method of claim 25 wherein said main light source image is focused in or near said eye's entrance pupil plane.

39. The method of claim 25 wherein said main light source image is focused in or near said eye's anterior focal plane.

40. The method of claim 25 wherein said main light source image is diffuse and of uniform intensity.

41. The method of claim 25 wherein said corrections in step (o) of said position reports are determined by a human operator.

42. The method of claim 25 wherein said corrections in step (o) of said position reports are determined by an automatic computer.

43. An apparatus for entoptically perceiving and mapping the white blood cell circulation and foveal area vasculature in the retina of a the human subject's eye under examination, the apparatus comprising:

(a) a means to establish and maintain translational alignment of said eye with said apparatus;

(b) a main light source which is imaged in or near the eye's entrance pupil, and a means of moving said main light source or its image along a main light path in space, said main light source being of variable intensity;

(c) a means of optically directing said main light image into said eye's entrance pupil, resulting in said eye's angle of retinal illumination changing with time;

(d) a means to image an aperture at optical infinity or other plane of interest to correct for any refractive error as an optical field stop for said apparatus, said aperture being of variable size;

(e) a fixation light source and a means to form a fixation light image on the retina of said eye, said fixation light source being of variable intensity;

(f) a tracking light source and a means to form a tracking light image on the retina of said eye, said tracking light source being of variable intensity;

(g) a means of moving said tracking light retinal image with respect to said fixation light retinal image;

(h) a means of transducing movement of said tracking light retinal image with respect to said fixation light retinal image to yield coordinates of its location on said retina with respect to location of said fixation light retinal image;

(i) a means of compiling or displaying said coordinates of tracking light image movement, said compilation or display comprising a map of said tracking light retinal image locations with respect to location of said fixation light retinal image;

(j) a means to detect and indicate magnitude and direction of translation of said eye with respect to said apparatus;

(k) a blue-field light source and a means to illuminate said eye's retina with said blue-field light source, said blue-field light source being of variable intensity;

(l) a speed-comparator light source casting an image and a means to form a retinal image of said speed-comparator light on said eye's retina, said speed-comparator light source being of variable intensity and said speed-comparator light source retinal image being of a size about equal to said entoptically perceived white blood cells;

(m) a means of causing said speed-comparator retinal image to move along a path on said eye's retina at a fixed velocity, said path and velocity being variable; and (n) a means of rotating and translating said speed comparator light retinal image on said eye's retina.

44. The apparatus of claim 43 wherein said main light path image space is circular, about 2 to 6 mm in diameter and about centered in the eye's pupil.

45. The apparatus of claim 43 wherein said main light path image space is circular, 4 mm in diameter and about centered in the eye's pupil.

46. The apparatus of claim 43 wherein said main light path is circular, being retraced at the rate of about 0.5 to 10 Hz.

47. The apparatus of claim 43 wherein said main light path is circular, being retraced at the rate of 3.5 Hz.

48. The apparatus of claim 43 wherein said aperture is that of an adjustable iris diaphragm.

49. The apparatus of claim 43 wherein said area of retinal illumination comprise a circle and said fixation light retinal image is within said circle.

50. The apparatus of claim 43 wherein said area of retinal illumination comprises a circle and said fixation light retinal image is centered within said circle.

51. The apparatus of claim 43 wherein said main light source has a peak wavelength of between about 430 nm and 555 nm and a half band pass of about +/− 60 nm.

52. The apparatus of claim 43 wherein said main light source has a peak wavelength of about 470 nm and a half band pass of about +/− 60 nm.

53. The apparatus of claim 43 wherein said main light source image is circular with a diameter of about 0.5 to 3 mm.

54. The apparatus of claim 43 wherein said main light source image is circular with a diameter of about 1.0 mm or less.

55. The apparatus of claim 43 wherein said main light source is imaged in or near said eye's entrance pupil plane.

56. The apparatus of claim 43 wherein said main light source is imaged in or near said eye's anterior focal plane.

57. The apparatus of claim 43 wherein said main light source image is diffuse and of uniform intensity.

58. The apparatus of claim 43 where in step (j) said indication of magnitude and direction of translation of said eye with respect to said apparatus is visible.

59. The apparatus of claim 43 where in step (j) said indication of magnitude and direction of translation of said eye with respect to said apparatus is sensed by an external operator.

60. The apparatus of claim 43 where in step (j) said indication of magnitude and direction of translation of said eye with respect to said apparatus is sensed by an external computer.

61. The apparatus of claim 43 wherein said tracking light retinal image coordinates of step (h) are corrected manually for retina image translation caused by translation of said eye with respect to said apparatus.

62. The apparatus of claim 43 wherein said tracking light retinal image coordinates of step (h) are corrected by automatic computation for retinal image translation caused by translation of said eye with respect to said apparatus.

63. The apparatus of claim 43 wherein said tracking light retinal image coordinates of step (h) are calibrated in units of length measured on said retinal surface.

64. The apparatus of claim 43 wherein said tracking light retinal image coordinates of step (h) are calibrated in units of angular subtense.

65. The apparatus of claim 43 wherein said means of moving said tracking light retinal image of step (h) is a joy stick or similar x-y manual controller.

66. The apparatus of claim 43 wherein said blue-field light source has a dominant wavelength of about 430 to 500 nm.

67. The apparatus of claim 43 wherein light from said blue-field light source is directed coaxially with the instrument's optical axis.

68. The apparatus of claim 43 wherein said blue-field light source comprises about 50% of total light.

69. The apparatus of claim 43 wherein said blue-field light is applied to said retina constantly or intermittently in alternation with the eccentric moving light source at a rate of 40 to 70 Hz, the duty angle being variable to optimize perception of both the retinal vessels and the white blood cells.

70. The apparatus of claim 43 wherein said retinal path of said speed-comparator light image is curved to mimic the course of a retinal vessel.

71. The apparatus of claim 43 wherein said retinal path of said speed-comparator light image is straight.

72. The apparatus of claim 43 wherein said retinal path of said speed-comparator light image is about $10^{-3}$ to $10^{-2}$ m in length.

73. The apparatus of claim 43 wherein said velocity of the speed comparator can be adjusted to mimic velocity of a white corpuscle passing through vasculature.

74. A method for entoptically perceiving and mapping the white blood cell circulation and foveal area vasculature in the retina of the eye of a human subject under examination with respect to the retinal point of fixation of said eye, the method comprising:

(a) optically directing an image of a main light source within or near said eye's entrance pupil so as to illuminate a portion of said eye's retina defined by a field stop, said main light source image being of variable intensity;

(b) causing said main light image to move along a main light path in space, said path resulting in said eye's retinal illumination angle changing with time;

(c) optically directing a fixation light source on said retina, resulting in the formation of a fixation light retinal image, said fixation light source being of variable intensity;

(d) having said subject visually fixate on said fixation light retinal image;

(e) having said subject provide descriptions of entoptically perceived vascular features of interest near said eye's foveal area;

(f) optically directing a tracking light source on said eye's retina, resulting in the formation of a tracking light retinal image, said tracking light retinal image being movable over said retinal surface with respect to said fixation light retinal image through a tracking light image controller operated by said subject;

(g) computing scaled outputs of said tracking light image controller to correspond to distances and angles measured on said retinal surface;

(h) having said subject move said tracking light retinal image along or around said entoptically perceived vascular features of interest while said subject maintains constant translational and rotational alignment of said eye with said fixation light retinal image;

(i) using said scaled outputs of said tracking light retinal image controller to create position reports of said entoptically perceived vascular features of interest on said retina;

(j) combining said position reports with said descriptions of said subject's entoptically perceived vascular features of interest to create a retinal map;

(k) observing said eye to detect misalignment with the instrumentation or said fixation light retinal image due to any combination of translation or rotation of said eye with respect to said fixation light retinal image;

(l) determining corrections required to said position reports resulting from said misalignment of said eye;

(m) applying said corrections to said position reports;

(n) illuminating said eye's retina in alternation with said main light source or constantly with a blue-field light source, said blue-field light source being of variable intensity and, if alternating, having a duty cycle of less than 100%;

(o) having said subject report entoptic perception of said white blood cell circulation;

(p) causing said fixation light and tracking light images to be viewed by said eye through an optical field stop aperture, said aperture being imaged at infinity or other plane of interest; and (q) having said subject adjust one or both of intensity and duty cycle of said light sources for best entoptic perception;

75. The method of claim 74 wherein said main light path in space is circular.

76. The method of claim 74 wherein said main light path in image space is circular, about 2 to 6 mm in diameter, and about centered in the eye's pupil.

77. The method of claim 74 wherein said main light path in image space is circular and 4 mm in diameter and about centered in the eye's pupil.

78. The method of claim 74 wherein said main light path in space is circular, being retraced at the rate of about 0.5 to 10 Hz.

79. The method of claim 74 wherein said main light path in space is circular, being retraced at the rate of about 3.5 Hz.

80. The method of claim 74 wherein said aperture stop of step (p) is that of an adjustable iris diaphragm.

81. The method of claim 74 wherein said illuminated portions of said eye's retina by said main light source in step (a) comprise a circle and said fixation light retinal image is within said circle.

82. The method of claim 74 wherein illuminated portions of said eye's retina by said main light source comprise a circle and said fixation light retinal image is centered within said circle.

83. The method of claim 74 wherein said main light source has a peak wavelength of between 430 nm and 555 nm and a half band pass of about +/− 60 nm.

84. The method of claim 74 wherein said main light source has a peak wavelength of about 470 nm and a half band pass of about +/− 60 nm.

85. The method of claim 74 wherein said main light source image is circular with a diameter of 0.5 to 3 mm.

86. The method of claim 74 wherein said main light source image is circular with a diameter of about 1.0 mm or less.

87. The method of claim 74 wherein said main light source image is focused in or near said eye's entrance pupil plane.

88. The method of claim 74 wherein said main light source image is focused in or near said eye's anterior focal plane.

89. The method of claim 74 wherein said main light source image is diffuse and of uniform intensity.

90. The method of claim 74 wherein said determining of corrections of said position reports is made by a human operator.

91. The method of claim 74 wherein said determining of corrections of said position reports is made by an automatic computer.

92. The method of claim 74 wherein application of said corrections to position reports is made by a human operator.

93. The method of claim 74 wherein application of said corrections to position reports is made by an automatic computer.

* * * * *

UNITED STATES PATENT AND TRADEMARK OFFICE
CERTIFICATE OF CORRECTION

PATENT NO.  : 5,016,643
DATED       : May 21, 1991
INVENTOR(S) : Raymond A Applegate, San Antonio, TX; Arthur Bradley, Bloomington, IN It is certified that error appears in the above-identified patent and that said Letters Patent is hereby corrected as shown below:

In claim 1, column 20, line 27 after 'plane' insert -- to form a main light source image -- ; line 31, after 'light' insert -- source --; line 43 between 'said and 'source' insert -- tracking light --.

In claim 5, column 21, line 5 before 'path' insert -- image --.

In claim 6, column 21, line 8 before 'path' insert -- image --.

In claim 10, column 21, line 20 delete "about +/-" and insert therefor -- +/- about --.

In claim 17, column 21, line 38 delete "step".

In claim 18, column 21, line 41 delete "step".

In claim 19, column 21, line 45 delete "step".

In claim 20, column 21, line 50 delete "steps".

In claim 21, column 21, line 55 delete "steps".

In claim 22, column 21, line 60 delete "step".

UNITED STATES PATENT AND TRADEMARK OFFICE
CERTIFICATE OF CORRECTION

PATENT NO.   :   5,016,643
DATED        :   May 21, 1991
INVENTOR(S)  :   Raymond A Applegate, San Antonio, TX; Arthur Bradley, Bloomington, IN It is certified that error appears in the above-identified patent and that said Letters Patent is hereby corrected as shown below:

```
In claim 23, column 21, line 63 delete "step".

In claim 25, column 22, line 16 delete "source" and insert
     therefor -- retinal --; line 19 delete "source" and
     insert therefor -- retinal --; line 25 delete "source"
     and insert therefor -- retinal --; line 31 delete
     "source" and insert therefore -- retinal --; line 33
     after 'light' insert -- source image --.

In claim 27, column 22, line 67 delete "image".

In claim 28, column 23, line 2 delete "image".

In claim 34, column 23, line 20 delete "about +/-" and
     insert therefor -- +/- about --.

In claim 35, column 23, line 23 between 'of' and 'about'
     insert -- +/- -- .

In claim 43, column 23, line 51 after 'pupil' insert -- to
     form a main light source image --; line 56 before
     'image' insert -- source --; column 24, line 10 between
     'light' and 'image' insert -- retinal --;
```

UNITED STATES PATENT AND TRADEMARK OFFICE
CERTIFICATE OF CORRECTION

PATENT NO. : 5,016,643
DATED : May 21, 1991
INVENTOR(S) : Raymond A Applegate, San Antonio, TX; Arthur Bradley, Bloomington, IN It is certified that error appears in the above-identified patent and that said Letters Patent is hereby corrected as shown below:

In claim 43, column 24; line 25 delete "source"; line 28 between 'speed-comparator' and 'retinal' insert -- light --; lines 32-33 delete "speed comparator" and insert therefor -- speed-comparator --.

In claim 44, column 24, line 35 delete "image" and insert therefor -- in --.

In claim 45, column 24, line 38 delete "image" and insert therefor -- in --.

In claim 46, column 24, line 41 after 'path' insert -- in space --.

In claim 47, column 24, line 44 after 'path' insert -- in space --.

In claim 49, column 24, line 48 delete "comprise" and insert therefor -- comprises --.

UNITED STATES PATENT AND TRADEMARK OFFICE
CERTIFICATE OF CORRECTION

Page 4 of 6

PATENT NO. : 5,016,643
DATED : May 21, 1991
INVENTOR(S) : Raymond A. Applegate, San Antonio, TX; Arthur Bradley, Bloomington, IN It is certified that error appears in the above-identified patent and that said Letters Patent is hereby corrected as shown below:

```
In claim 51, column 24, line 55 delete "about +/-" and
    insert therefor -- +/- about --.
In claim 52, column 24, line 58 delete "about +/-" and
    insert therefor -- +/- about --.
In claim 58, column 25, line 6 delete "step".
In claim 59, column 25, line 9 delete "step".
In claim 60, column 25, line 13 delete "step".
In claim 61, column 25, line 18 delete "step".
In claim 62, column 25, line 22 delete "step".
In claim 63, column 25, line 27 delete "step".
In claim 64, column 25, line 30 delete "step".
In claim 65, column 25, line 33 delete "step".
In claim 69, column 25, line 44 after 'light' insert
    -- source --.
In claim 73, column 25, line 58 delete "speed comparator"
    and insert therefor -- speed-comparator --.
```

UNITED STATES PATENT AND TRADEMARK OFFICE
CERTIFICATE OF CORRECTION

PATENT NO. : 5,016,643

DATED : May 21, 1991

INVENTOR(S) : Raymond A. Applegate, San Antonio, TX; Arthur Bradley, Bloomington, IN It is certified that error appears in the above-identified patent and that said Letters Patent is hereby corrected as shown below:

In claim 74, column 26, line 3 after 'light' insert
-- source --; line 60 after 'perception' delete ";" and
insert therefor -- . --.

In claim 76, column 26, line 64 delete "image".

In claim 77, column 26, line 67 delete "image".

In claim 81, column 27, line 10 delete "portions" and insert
therefor -- portion --; line 11 delete "comprise" and
insert therefor -- comprises --.

UNITED STATES PATENT AND TRADEMARK OFFICE
CERTIFICATE OF CORRECTION

PATENT NO.   : 5,016,643
DATED        : May 21, 1991
INVENTOR(S)  : Raymond A. Applegate, et al It is certified that error appears in the above-identified patent and that said Letters Patent is hereby corrected as shown below:

In claim 82, column 27, line 14 delete "portions" and insert therefor -- portion --; lines 14-15 delete "comprise" and insert therefor -- comprises --.

In claim 83, column 27, line 19 delete "about +/-" and insert therefor -- +/- about --.

In claim 84, column 27, line 22 delete "about +/-" and insert therefor -- +/- about --.

Signed and Sealed this

Thirteenth Day of October, 1992

*Attest:*

DOUGLAS B. COMER

*Attesting Officer*      *Acting Commissioner of Patents and Trademarks*